(12) United States Patent
Peritt et al.

(10) Patent No.: US 10,940,259 B2
(45) Date of Patent: *Mar. 9, 2021

(54) PROCESSING BLOOD

(71) Applicant: Mallinckrodt Hospital Products IP Limited, Dublin (IE)

(72) Inventors: David Peritt, Skokie, IL (US); Philip Wong, Cremorne (AU); Janet Lesley Macpherson, Leichhardt (AU); Kevin Henrichsen, Shamong, NJ (US); Geoffrey Phillip Symonds, Rose Bay (AU); Susan Pond, Kirribilli (AU)

(73) Assignee: Mallinckrodt Hospital Products IP Limited, Dublin (IE)

( * ) Notice: Subject to any disclaimer, the term of this patent is extended or adjusted under 35 U.S.C. 154(b) by 182 days.

This patent is subject to a terminal disclaimer.

(21) Appl. No.: 16/171,089

(22) Filed: Oct. 25, 2018

(65) Prior Publication Data
US 2019/0060548 A1 Feb. 28, 2019

Related U.S. Application Data

(60) Continuation of application No. 15/974,881, filed on May 9, 2018, which is a division of application No. (Continued)

(51) Int. Cl.
*A61M 1/34* (2006.01)
*A61M 1/38* (2006.01)
(Continued)

(52) U.S. Cl.
CPC .......... *A61M 1/3496* (2013.01); *A61M 1/362* (2014.02); *A61M 1/3616* (2014.02);
(Continued)

(58) Field of Classification Search
CPC .. A61M 1/302; A61M 1/3675; A61M 1/3696; A61M 1/3496; A61M 1/362;
(Continued)

(56) References Cited

U.S. PATENT DOCUMENTS 4,303,193 A 12/1981 Latham, Jr.
4,614,590 A 9/1986 Rath
(Continued)

FOREIGN PATENT DOCUMENTS

DE 29713774 U1 1/1998
EP 0421380 4/1994
(Continued)

OTHER PUBLICATIONS

Takahashi, Tuyoshi, "Vaccination of chronic myelogenous leukemia patients with peptide-pulsed dendritic cells", Jpn. J. Clin. Immun., vol. 22, No. 6, pp. 452-456, 1999, Japan.
(Continued)

*Primary Examiner* — Philip R Wiest

(57) ABSTRACT

Methods (300), devices, and systems of processing blood are described. The method (300) comprises the steps of: obtaining (312) blood from a patient coupled to a single blood processing device to form a closed loop between the patient and the blood processing device; collecting (314) bulk mononuclear blood cells from the blood by leukapheresis implemented using the blood processing device in the closed loop; and enriching (316) concurrently target cells separated from non-target cells in the bulk mononuclear blood cells using the blood processing device in the closed loop.

24 Claims, 12 Drawing Sheets

Related U.S. Application Data

15/066,659, filed on Mar. 10, 2016, now abandoned, which is a continuation of application No. 13/738,039, filed on Jan. 10, 2013, now abandoned, which is a continuation of application No. 12/628,303, filed on Dec. 1, 2009, now abandoned.

(60) Provisional application No. 61/140,196, filed on Dec. 23, 2008.

(51) Int. Cl.
    *A61M 1/36*     (2006.01)
    *B03C 1/015*     (2006.01)
    *B04B 5/10*     (2006.01)
    *B04B 11/02*     (2006.01)

(52) U.S. Cl.
CPC ........ *A61M 1/3626* (2013.01); *A61M 1/3672* (2013.01); *A61M 1/3689* (2014.02); *A61M 1/3696* (2014.02); *A61M 1/38* (2013.01); *B03C 1/015* (2013.01); *B04B 5/10* (2013.01); *B04B 11/02* (2013.01); *A61M 2202/0064* (2013.01); *A61M 2202/0439* (2013.01)

(58) Field of Classification Search
CPC .............. A61M 1/3689; A61M 1/3626; A61M 1/3672; A61M 1/38; A61M 2202/0439; B03C 1/015; B04B 5/10; B04B 11/02
See application file for complete search history.

(56) References Cited

U.S. PATENT DOCUMENTS

| | | | |
|---|---|---|---|
| 5,811,275 | A | 9/1998 | Wong-Staal et al. |
| 5,984,887 | A | 11/1999 | McLaughlin et al. |
| 6,544,751 | B1 | 4/2003 | Brandwein |
| 6,610,002 | B2 | 8/2003 | Dolecek |
| 7,169,547 | B2 | 1/2007 | Rubenstein |
| 7,186,230 | B2 | 3/2007 | Briggs et al. |
| 7,211,037 | B2 | 5/2007 | Briggs et al. |
| 2002/0107469 | A1* | 8/2002 | Bolan ................. A61M 1/3675 604/6.01 |
| 2004/0042041 | A1 | 3/2004 | Yun |
| 2005/0173315 | A1* | 8/2005 | Bosch ................. A61M 1/3603 210/97 |
| 2017/0096636 | A1 | 4/2017 | McIver et al. |
| 2018/0256806 | A1* | 9/2018 | Peritt ................. A61M 1/3626 |
| 2019/0060548 | A1 | 2/2019 | Peritt |
| 2019/0060549 | A1* | 2/2019 | Peritt ................. A61M 1/3696 |

FOREIGN PATENT DOCUMENTS

| | | |
|---|---|---|
| WO | 1995/024969 A1 | 9/1995 |
| WO | 1996/009068 A1 | 3/1996 |
| WO | 2002/094350 A2 | 11/2002 |
| WO | 2003/006691 A1 | 1/2003 |
| WO | 2004/000444 A1 | 12/2003 |
| WO | 2004/042041 A1 | 5/2004 |

OTHER PUBLICATIONS

Amado, R.G. et al., "Anti-human immunodeficiency virus hematopoietic progenitor cell-delivered ribozyme in a phase I study; myeloid and lymphoid reconstitution in human immunodeficiency virus type-1-infected patients", Human Gene Therapy, 15:251-262 (2004).

Battye, F.L. et al., "Flow cytometry and cell-separation procedures", CLUT. Opin. Immunol., 3:239-241 (1991).

Dudley, M.E. et al., "Cancer regression and autoimmunity in patients after clonal repopulation with antitumor lymphocytes", Science, 298:850-854 (2002).

Edelson, R.L., "Photopheresis: a new therapeutic concept", Yale J Biol Med., 62:565-577 (1989).

Gryn, J. et al., "Factors affecting purification of CD34+ peripheral blood stem cells using the Baxter Isolex 300i", Journal of Hematotherapy & Stem Cell Research, (11):719-730 (2002).

June, C.H. et al., "Clinical application of expanded CD4+25+ cells", Semin. Immunol., 18:78-88 (2006).

June, C.H., "Adoptive T cell therapy for cancer in the clinic", J Clin Invest., 117(6):1466-1476 (2007).

Meehan, K.R. et al., "Mobilization, collection, and processing of autologous peripheral blood stem cells: Development of a clinical process with associated costs", Journal of Hematotherapy & Stem Cell Research,9(5):767-771 (2000).

Moog, R., "Apheresis techniques for collection of peripheral blood progenitor cells", Transfusion and Apheresis Science, 31:207-220 (2004).

Reddy, R.L., "Mobilization and collection of peripheral blood progenitor cells for transplantation", Transfusion and Apheresis Science, 32:63-72 (2005).

Sevilla, J. et al., "Risks and methods for peripheral blood progenitor cell collection in small children", Transfusion and Apheresis Science, 31:221-231 (2004).

Steinman, R.M. et al., "Taking dendritic cells into medicine", Nature, 449:419-26 (2007).

Stock, P. et al., "Inhibition of the allergic response by regulatory T cells", Curr. Opin. Allergy Clin. Immunol.. 6:12-16 ;2006).

Witt, V. et al., "Collection efficiencies of MNC subpopulations during autologous CD34+ peripheral blood progenitor : ell (PBPC) harvests in small children and adolescents", Journal of Clinical Apheresis, 16:161-168 (2001).

Yamaguchi, E. et al., "Kinetics of peripheral blood stem cell collection in large-volume leukapheresis for pediatric patients undergoing chemotherapy and adult patients before chemotherapy", Journal of Hematotherapy & Stem Cell Research, 9:565-572 (2000).

Office Action issued for Mexican Application No. MX/A/2011/006767 dated Feb. 19, 2015 (English translation), 3 pages.

Office Action issued for Indian Application No. 2461/KOLNP/2011 dated Jul. 18, 2018, 9 pages.

Office action dated Jun. 24, 2020 in related U.S. Appl. No. 15/974,881, 9 pages.

Office action dated Jul. 23, 2020 in related U.S. Appl. No. 16/171,089, 10 pages.

Office action dated Jun. 24, 2020 from related U.S. Appl. No. 15/974,881, 9 pages.

Office action dated Jul. 23, 2020 from related U.S. Appl. No. 16/171,096 , 10 pages.

\* cited by examiner

PROCESSING BLOOD

CROSS-REFERENCE TO RELATED APPLICATIONS

This application is a continuation of pending U.S. patent application Ser. No. 15/974,881 filed May 9, 2018 which is a division of Ser. No. 15/066,659 filed Mar. 10, 2016 which is a continuation of Ser. No. 13/738,039 filed Jan. 10, 2013 now abandoned which is a continuation of Ser. No. 12/628,303 filed Dec. 1, 2009 now abandoned which claims priority from U.S. Provisional Application No. 61/140,196 filed Dec. 23, 2008, the contents of which are incorporated by reference herein in their entirety.

TECHNICAL FIELD

The present invention generally relates to methods and apparatuses for processing blood and more particularly to methods and devices for leukapheresis.

BACKGROUND

Blood cells are produced continuously over the life of an individual and derive from the most primitive blood cell, the so-called hematopoietic stem cell (HSC). This HSC is able to give rise to hematopoietic progenitor cells (HPC) and to blood cells of the various cell types (eg red blood cells (RBC) and leukocytes or white blood cells (WBC)) and tends to be found in the bone marrow. The more mature blood cell types are found in the blood and lymphatic tissue. Hematopoiesis is the continuous production of blood cells in the individual from HSC and HPC. This results in the peripheral blood having many different types of blood cells of the various myeloid and lymphoid lineages and of varying degrees of maturity. These blood cells are responsible for physiological processes such as oxygen transport by red blood cells, immune function by dendritic cells, B and T lymphocytes, and inflammatory response by granulocytes and macrophages.

Apheresis is a medical procedure in which the blood of an individual is passed through an apparatus, yielding a predominant constituent (e.g. mononuclear cells), and returning the other constituents to the circulation. Apheresis is in general a three-step process comprising: (1) withdrawing blood from the individual, (2) separating the blood components (e.g. based on density), and (3) returning certain component(s) of the blood to the individual. The blood is normally separated into three fractions: RBC (about 45% of total blood), "buffy coat" (less than 1% of total blood) and plasma (about 55% of total blood). Various types of apheresis procedures can be used depending on the component of blood that is being removed. For example, "plasmapheresis" generally refers to the separation and collection of blood plasma and "thrombocytapheresis" refers to the separation and collection of platelets, while "leukapheresis" usually refers to the separation and collection of leukocytes (WBC).

With the advance of medical sciences, apheresis can be carried out in a patient-connected, closed-loop continuous-flow manner. Devices used for this purpose include, for example, the following apheresis systems: COBE® Spectra, Trima, Spectra Optia systems (all marketed by Gambro BCT) and the Amicus and CS-3000+ (marketed by Fenwal/Baxter).

Recently, leukapheresis is also being utilised to collect a certain fraction of blood mononuclear cells (MNC) for use in bone marrow transplantation and other disease areas. For example, patients who have been ablated to treat a malignancy can be infused with a bulk population of donor mononuclear cells that contain HSC and HPC (those present in peripheral blood, also being referred as peripheral blood progenitor cells, or PBPC), to effect subsequent reconstitution of their hematopoietic system. In this instance, the buffy coat (containing the majority of the WBC (granulocytes, lymphocytes, monocytes), PBPC and some platelets) is first collected while the remaining components of blood (including plasma, RBC, platelets and some WBC) are returned to the individual. The PBPC are then enriched and isolated, while the remaining fraction of the buffy coat (constituting nearly 99% of the buffy coat) is discarded. This process of cell enrichment (i.e. cell isolation and purification) is currently carried out in a patient-disconnected manner, using separate devices to those of the apheresis machines. Devices used for this purpose include, for example, the Baxter Isolex 300i and the Miltenyi CliniMACS, which enrich PBPC based on a specific ligand (CD34, both devices and CD133 Miltenyi) on the cells' surface. Other stand-alone devices, such as the Gambro COBE 2991 Blood Cell Processor or the Baxter CytoMate™ Cell Washing System is often used to wash, concentrate, or place the cells into appropriate growth or infusion medium.

In a further application, leukapheresis can be used to treat an individual's WBC in a process called photopheresis (Edelson et al., Yale J Biol Med. 1989 November-December; 62(6): 565-77). In this process, the individual first receives a dose of photoactivatable substance (e.g. 8 methoxy-psoralen). Then apheresis is carried out in which the WBC of the individual is irradiated with Ultraviolet A (UVA) light, resulting in the activation of the substance and inhibition of the metabolic processes of the WBC. Devices used for this purpose include, for example, the UVAR AND UVAR® XTS™ Photopheresis System (marketed by Therakos).

In addition to the enrichment process described above, the PBPC collected may also be modified in further processes before re-infusing back to the individual. This is generally effected by the use of a variety of techniques in cell culture. Ultimately, the modified cells (for example, altered phenotype, genotype or activity) may be re-introduced into the patient for certain therapeutic benefits. Examples of modification processes include the production of HSC/HPC containing an anti-HIV gene (R. G. Amado. et al. Human Gene Therapy 15 (2004), 251-262) and the production of cytotoxic T lymphocytes 'educated' to home to and kill specific tumours.

FIG. 1 is a block diagram illustrating the current means by which blood is removed from a patient, processed and returned. Here, an arrangement 100 of devices that can be sequentially used for cell collection employing leukapheresis and cell enrichment techniques, such as using cell washing, purification. The diagram also lists optional cell modifications. Exemplary devices that can be used in this method include the Cobe Spectra device. Such a device, 110, for leukapheresis (collection), is used sequentially with a cell-washing device, such as a Baxter CytoMate device, 120, (enrichment) which is further used with a cell purification (enrichment) device such as a Baxter Isolex 300i device, 130. In addition, cell manipulation (modification) devices, 140, can be employed in this scheme and include, but are not limited to: electroporation, lipofection, viral transduction, light (UVA, UVB, etc.), addition of drugs, cell activation, pressure, heating functions, etc. The bag 150 of processed blood cells produced as the output of devices 110, 120, 130, and 140 are provided to the patient 160 for return of the processed blood.

FIG. 2 depicts a specific example of a method 300 for cell collection, enrichment and modification. The example is of a method used for the introduction of an anti-HIV gene into CD34+ HSC/HPC in which over a 5 day period:

In step 310, mononuclear cells are collected, i.e. harvested by leukapheresis. In this step 310, other blood cell components, namely red blood cells, platelets, plasma and polymorphonuclear cells are returned to the patient.

In step 320, the mononuclear cell fraction is washed using, for example, a CytoMate (referenced above) (day 2), target CD34+ cells are enriched using, for example, an Isolex 300i device (day 2), and non-CD34+ cells are discarded.

In step 330, the CD34+ cells are cultured in the presence of cytokines (day 2), and the anti-HIV gene (a ribozyme against a conserved region of the tat/vpr gene) is introduced using a murine retrovirus (day 4).

After step 330, the product release testing is performed (day 5), and the cells are infused to the same individual, who was originally leukapheresed.

However, apheresis has inherent drawbacks and limitations. For example, apheresis is only a fluid constituent(s) collection procedure. Despite technological advances, the composite steps of collection, enrichment and (optional) modification of target blood cells are conducted by using separate continuous and discontinuous devices, as mentioned hereinbefore. Of these steps, only collection and in one instance, collection and modification (photopheresis) are currently patient-connected. These current discontinuous processes are time consuming and materials, labor and costs inefficient (J. Gryn et al., Journal of Hematotherapy & Stem Cell Research 11 (2002), 719-730; K. R. Meehan et al., Journal of Hematotherapy & Stem Cell Research 9 (2000), 767-771). These processes also introduce serious concerns such as (i) safety due to potential microbial contamination and (ii) chain of custody (i.e. ensuring the correct cells are returned to the patient and maintaining the cells' integrity) due to the logistics of cell selection and modification. For instance, hemolysis is a rare complication due to kinks in the lines of the apheresis collection kits (R. Reddy, Transfusion and Apheresis Science 32 (2005) 63-72).

To further illustrate, thrombocytopenia (depletion of platelets) is a well-known unwanted result of leukapheresis and the most frequently reported secondary effect of leukapheresis in children (J. Sevilla et al., Transfusion and Apheresis Science 31 (2004) 221-231; E. Yamaguchi et al., Journal of Hematotherapy & Stem Cell Research 9 (2000) 565-572). Thrombocytopenia is important, because patients are often thrombocytopenic due to their underlying diseases and there is an additional loss of platelets during leukapheresis. Ideally, in individuals with a deficiency in platelet numbers due to certain disease states, the apheresed platelets within the buffy coat should be separated and returned to the individual. In reality, however, the apheresed platelets are simply discarded as wastes. This aside, the reduction of platelets in the buffy coat also has the added benefit of increasing the efficiency of immunoaffinity selection of CD34+ progenitor cells (a type of PBPC) by a mean of 1.8 fold (R. Moog, Transfusion and Apheresis Science 31 (2004) 207-220).

Another drawback of the leukapheresis process is the loss of valuable lymphocytes for some patients. As discussed hereinbefore, HSC and HPC (in particular CD34+ progenitor cells) are often selected for use to effect reconstitution of an individual's hematopoietic system. For human immunodeficiency virus (HIV) infected individuals, the selection of CD34+ progenitor cells—using leukapheresis rid their body of valuable lymphocytes (such as CD3+ and CD4+ cells), which are often already low in numbers. CD34+ progenitor cells—around 1.3% after mobilization—are among the smallest cell fraction collected during PBPC leukapheresis whereas lymphocytes and monocytes account for up to 70% of the apheresis products (V. Witt et at., Journal of Clinical Apheresis 16 (2001) 161-168).

A need exists for a device that can overcome or at least ameliorate one or more disadvantages of existing systems, including those mentioned hereinbefore.

SUMMARY

In accordance with an aspect of the invention, there is provided an apparatus for processing blood. The apparatus comprises: an inlet interface for coupling with a patient to receive blood directly from the circulation of the patient; a leukapheresis module coupled to the inlet interface for collecting bulk mononuclear blood cells from the received blood; an enrichment module coupled to the leukapheresis module for enriching concurrently target cells separated from non-target cells in the bulk mononuclear blood cells; an outlet interface coupled to at least one of the leukapheresis module and the enrichment module for coupling with the patient to return enriched target cells to the circulation of the patient, the apparatus and the patient forming a closed loop when coupled together; and a controller for automated control of operation of the inlet and outlet interfaces, the leukapheresis module, and the enrichment module.

In accordance with another aspect of the invention, there is provided a method of processing blood. The method comprises the steps of: obtaining blood from a patient coupled to a single blood processing device to form a closed loop between the patient and the blood processing device; collecting bulk mononuclear blood cells from the blood by leukapheresis implemented using the blood processing device in the closed loop; and enriching concurrently target cells separated from non-target cells in the bulk mononuclear blood cells using the blood processing device in the closed loop.

In accordance with a further aspect of the invention, there is provided a system for processing blood. The system comprises: a mechanism for obtaining blood from a patient and comprises a single blood processing device coupled to the obtaining means and the patient to form a closed loop between the patient and the blood processing device. The blood processing device comprises: a module for collecting bulk mononuclear blood cells from the blood by leukapheresis implemented using the blood processing device in the closed loop; and a module for enriching concurrently target cells separated from non-target cells in the bulk mononuclear blood cells using the blood processing device in the closed loop.

These and other aspects of the invention are set forth in greater detail hereinafter.

BRIEF DESCRIPTION OF THE DRAWINGS

Embodiments of the invention are described hereinafter with reference to the drawings, in which.

DETAILED DESCRIPTION

Figure 1:
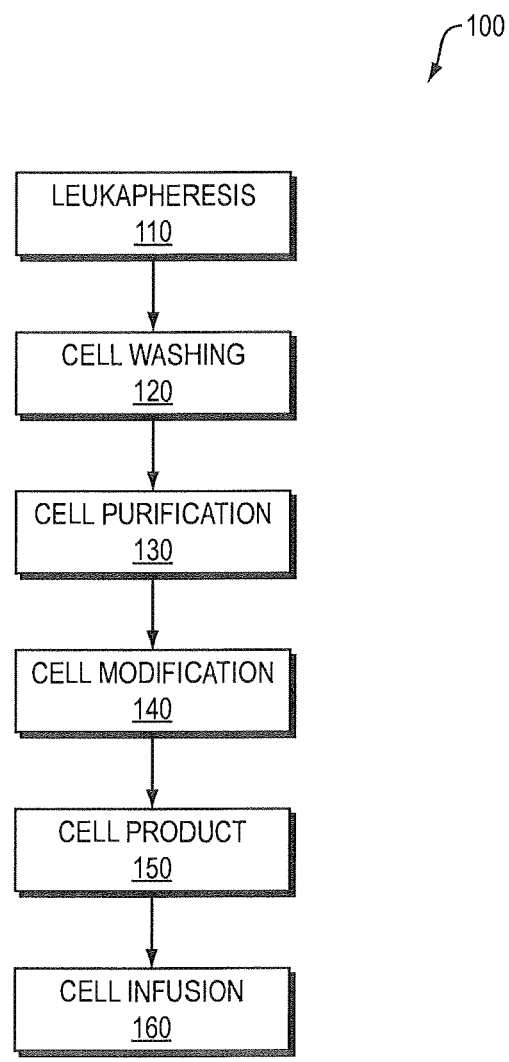
FIG. 1 is a block diagram of devices for cell collection by leukapheresis and enrichment using cell washing and purification.

Methods, apparatuses, and systems for processing blood cells are described hereinafter. In particular, methods, apparatuses, and systems are disclosed for leukapheresis that enable the concurrent collection and enrichment of specific target cells from an individual's peripheral blood and the remaining blood components are returned to the individual. Additionally, the target cells collected may be modified and returned to the individual during the apheresis process, or may be returned to the individual at a later time. The embodiments of the invention relate to a closed-loop device that enables the concurrent collection and enrichment of specific target cells from peripheral blood of an individual and return of the non-target cells to the individual. The target cells may be modified to alter their phenotype, genotype or activity and in an extension of the closed-loop returned to the individual. The embodiments of the invention efficiently carry out the process of apheresis in a patient-connected, closed-loop continuous-flow manner, whereby only target components of blood (e.g. CD34+ progenitor cells) are enriched while all other remaining components are returned to the patient. Additionally, certain other functions may be carried on the target cells (e.g. modifying the phenotype) with the option of returning the modified cells to the patient. The provision of such a device can significantly reduce operating costs (no need of multiple apparatus and consumables) and ensure product consistency. Enabling the apheresis procedure to occur in a single location in a single device also reduces the risk of damage or loss of the product.

However, from this disclosure, it will be apparent to those skilled in the art that modifications and/or substitutions may be made without departing from the scope and spirit of the invention.

Definitions

| Term | Definition |
|---|---|
| Bulk Mononuclear Cell | The bulk mononuclear cell population collected by leukapheresis. Also referred to as Bulk Mononuclear Cell Population. |
| Capture | The isolation of one specific cell type or types from a mixture of cells by a specific interaction (eg physical or chemical) (eg antibody-antigen or other interactions as described herein). This may be done by means of a cell capture system. |
| Cell Processing | All steps (some of which may be optional) that involve collecting, enriching, modifying and storing cells. The cells may be used outside the body for research, monitoring or discarded or they may be subsequently infused to an individual(s). |
| Closed-loop | At least a subsection of cells is kept in a system that is a continuous, such that the cells are derived from the patient and can be returned to the patient without being moved off-line. |
| Cluster Designation (CD) | Classification system for monoclonal antibodies generated by laboratories worldwide against cell surface molecules on leukocytes initially, now also antigens from other cell types. |
| Concurrent | Part of same real-time process, occurring in real time: it can be sequential or simultaneous. |
| Continuous | Part of a closed-loop. |
| Continuous flow | The flow of blood from the patient to the device and back to the patient in which non-target cells generally return to the patient whereas target cells may be collected, may flow past an enrichment system in the device, may be modified by a modification system in the device and then return to the patient: all in a closed-loop patient-connected manner and in real time. |
| Continuous Flow System | The fluid path and engineering controls that permit Continuous flow. |
| Differential Centrifugation | Centrifugation to separate a bulk population of cells on the basis of size and density. |
| Discontinuous | Not part of a closed-loop. |
| Enrich | The concentration of the target cell type by a physical or chemical means; this may encompass washing, isolation or purification, |
| Integral | An important part of/requirement. |
| Isolate | The process of extracting (eg by capture) one specific cell type or types from a mixture of cells, |
| Leukapheresis | A continuous flow process where blood is drawn from a donor and a bulk mononuclear cell population is collected and the remaining components of blood (plasma, platelets, red blood cells and polymorphonuclear cells) are re-infused to the donor. |
| Ligand | Any molecule (eg an antibody) that binds to another (eg a receptor). |
| Monitor | Determination of parameters of process (eg real-time or post-hoc) eg measurement of number of a specific cell type (eg CD34) being captured, |
| Non-Target Cells | These are the cells remaining after the enrichment of target cells from the bulk mononuclear cell collection, which has been collected by leukapheresis. |

-continued

| Term | Definition |
|---|---|
| Modification | The alteration of cell phenotype, genotype or activity; also referred to in some instances as manipulation. |
| Patient-connected | This refers to when the device is connected to the patient. The patient may be connected to the device for the entire period of blood cell collection and enrichment and potentially cell modification. The flow of blood is from the patient to the device and back to the patient in which non-target cells generally return to the patient whereas target cells may be collected, may flow past an enrichment system in the device, may be modified by a modification system in the device and then return to the patient; all in a closed-loop manner. |
| Patient-disconnected | Steps of cell processing that occur when the patient is disconnected from the device. |
| Purity | The percentage of a specific cell type in the cell population. |
| Real-Time | As it is occurring |
| Real-Time Monitoring | Determination of parameters of process as it is occurring eg measurement of number of a specific cell type (eg CD34) being captured. |
| Release | The process of separation (eg physical or chemical) of the cell from the capture system. |
| Same device | One device in which multiple functions may be performed. |
| Target Cell | The cell type or types enriched from the bulk mononuclear cell population collected by leukapheresis. The target cell type (or types) is enriched for subsequent discarding or for subsequent use which may include modification and re-infusion to the individual. It is understood that the target blood cell type that is enriched can encompass one or more cell types. Also referred to herein as Target Cell Type or Target Cell Population. |

Multi-functional devices and methods of use thereof, that is closed-loop, can be patient-connected and comprise the following aspects:

a) Collection: performing leukapheresis collection of a bulk mononuclear blood cell population that contains the target cell population of interest; and concurrently b) Enrichment: enriching a target cell population from the bulk mononuclear blood cell population The enriched target cell population is either returned to the patient, removed for subsequent off-line use including modifications that may involve the later infusion of the modified cells to the patient. The off-line use of the target cell population may include use for research or monitoring. The non-target cell population may be concurrently returned to the patient, removed off-line for use or optionally discarded. The method can additionally, in an extension of the closed-loop process, modify the target blood cell population before returning the modified target blood cell population to the patient.

Figure 3:
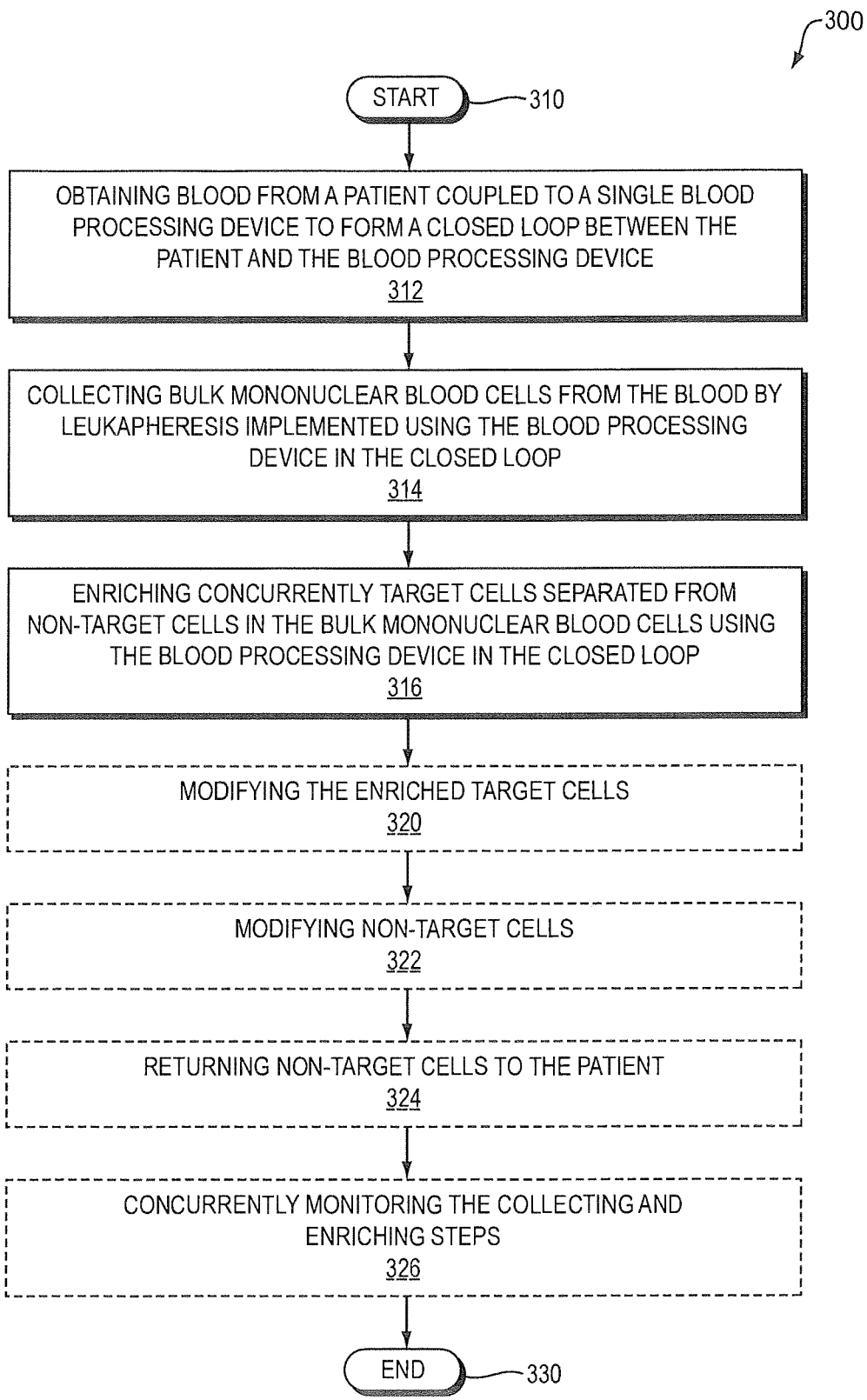
FIG. 3 is a flow diagram of a method of processing blood cells in accordance with an embodiment of the invention.

FIG. 3 depicts at a high level a method 300 of processing blood comprising steps 310-316 and 330 (indicated by boxes having unbroken lines). While not depicted in FIG. 3, the steps 312-316 may be carried out repeatedly. The method 300 may optionally comprise one or more of steps 320-326 (indicated by boxes having dashed lines in FIG. 3). Likewise, one or more of these steps 320-326 may be performed repeatedly (not shown in FIG. 3). While the steps of method 300 are depicted as being performed sequentially and in a particular order, the method 300 is not limited to the particular sequence, sequential processing, or all of the steps, some of which are optional, being performed. It will be understood by those skilled in the art that in the light of this disclosure the ordering of steps may be changed. Further, one or more steps may be performed in parallel. For example, steps 312 to 316 may be performed in parallel. Still further, step 326 may be performed in parallel with steps 314 and 316. The method 300 of processing blood is described in greater detail hereinafter.

Processing commences in step 310. In step 312, blood is obtained from a patient coupled to a single blood-processing device to form a closed loop between the patient and the blood processing device.

In step 314, bulk mononuclear blood cells are collected from the blood by leukapheresis implemented using the blood-processing device in the closed loop. The collecting step 314 may comprise using differential centrifugation to collect the mononuclear blood cells. The differential centrifugation may be conducted by a continuous flow system.

In step 316, target cells separated from non-target cells in the bulk mononuclear blood cells are enriched concurrently using the blood-processing device in the closed loop. The target cells may be B cells, T cells, dendritic cells, monocytes, neutrophils, natural killer (NK) cells, T regulatory cells, T helper cells, cytotoxic T lymphocytes (CTLs), hematopoietic stem cells (HSCs), hematopoietic progenitor cells, endothelial cells, epithelial cells, mesenchymal cells, lymphocytes, lymphokine activated killer cells (LAKs), or tumor infiltrating lymphocytes (TILs). The T cells may be enriched. The T cells may be CD8+ or CD4+. The hematopoietic progenitor cells and the hematopoietic stem cells may be enriched. The hematopoietic stem cells and the hematopoietic progenitor cells may be positive for one or more of CD34, CD133, and CD143. Alternatively, the target cells may be at least one of malignant cells from blood, malignant cells from tissue, virally infected cells, bacterially infected cells, at least one virus, at least one bacterium, a parasite, fetal cells, and pathogenic effector cells.

The enriching step 316 may comprise ligand capture to enrich the target cells. The ligand may be an antibody specific for a cell surface ligand. The cell surface ligand may be an epithelial cell adhesion molecule (EpCAM), a selectin, an adhesion molecule receptor, a homing receptor, a cytokine receptor, a chemokine receptor, or an enzyme. The cell surface ligand may be a cluster designation (CD) antigen. The CD antigen may be CD1a, CD4, CD8, CD14, CD25, CD34, CD133, or CD143. The target cell enrichment in step 316 may be effected by at least one of magnetics, fluorescent activated cell sorting, microfluidics, solid support, acoustics, bioluminescence, antibody tagging, and enzyme substrate. The solid support may comprise a particle. The particle may be at least one of a magnetic particle and a density modified particle.

The collecting and enriching steps 314, 316 may be performed in different sections of the blood-processing device.

In step 320, the enriched target cells may be modified. The modifying step 320 may involve modification comprising one or more of activation, expansion, induction of apoptosis, gene modification, and induction of antigen specificity. The modifying step 320 may involve modification that is effected by at least one of cross linking cell surface receptors, irradiation, and treatment with at least one of cytokines, chemokines, antigen stimulation, hormones, drugs, pressure, and heating. The irradiation may be at least one of gamma, beta, alpha, and light radiation. The light radiation may be at least one of ultraviolet A (UVA), ultraviolet B (UVB), and visible light. Alternatively, the modifying step 320 may involve genetic modification that is effected by one of transfection and transduction of genetic material into at least a portion of the target cells. Transfection of genetic material may be by one of electroporation and lipofection. Transduction of genetic material may be by viral vector transduction. In yet another alternative, the modifying step 320 may involve modification comprising at least one of cytotoxic T lymphocyte (CTL) activation, T regulatory cell (Treg) activation, and genetically modified blood cells protected from human immunodeficiency virus (HIV).

In step 322, non-target cells may be modified. Further, in step 324, the non-target cells may be returned to the patient. The non-target cells may be returned to the patient connected in the closed loop, or disconnected from the closed loop. Still further, the non-target cells may be discarded.

In step 326, the collecting and enriching steps may be monitored concurrently for cell number. This would allow the collection to be completed as soon as sufficient cells have been collected and enriched, allowing the collection to be tailored to the patient.

The method may comprise maintaining continuous connection of the patient in the closed loop during processing of the target cells, or disconnecting the patient from the closed loop for a time interval during processing of the target cells. Processing terminates (End) in step 330. These and other aspects are described in greater detail hereinafter.

Figure 4:
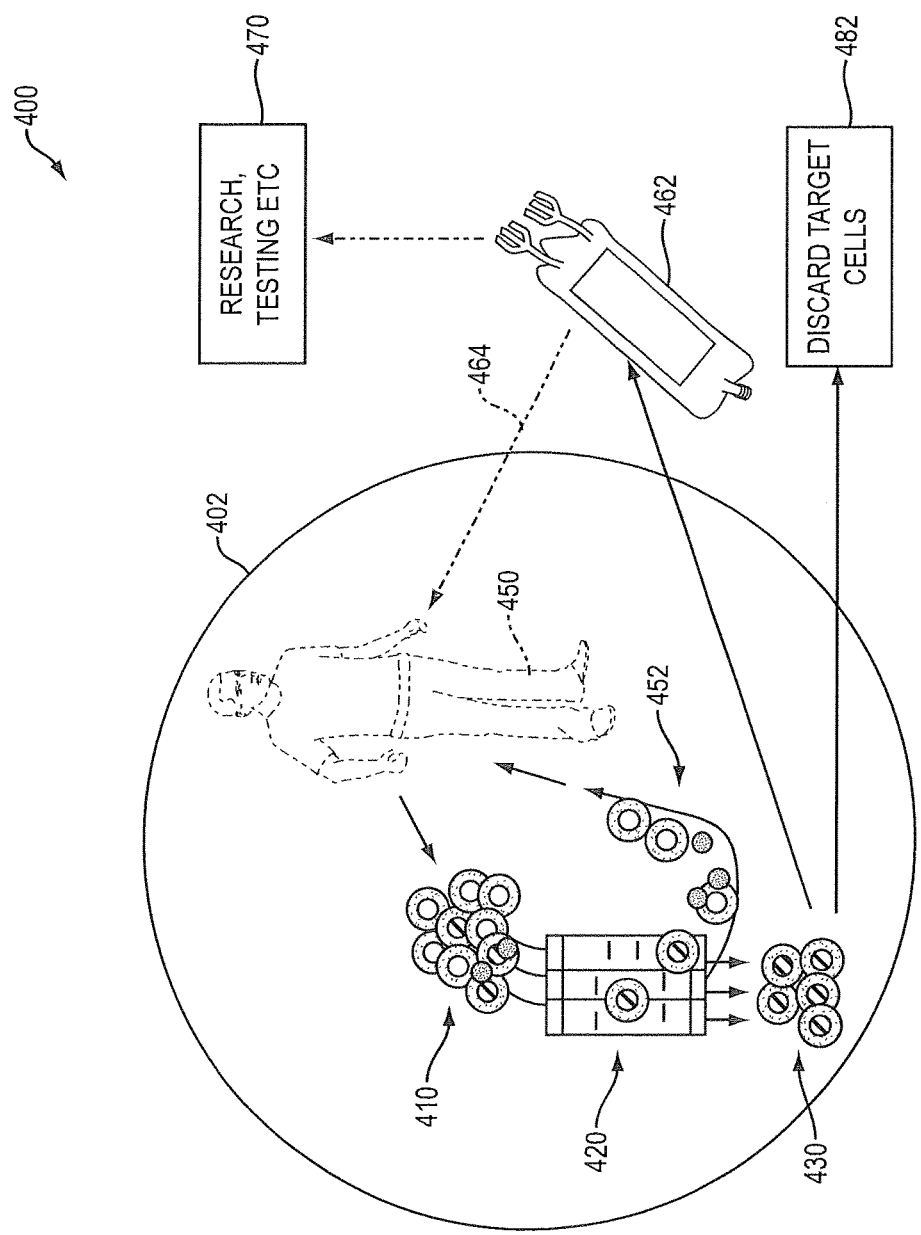
FIG. 4 is a schematic diagram depicting concurrent cell collection, target cell enrichment and return of non-target cells.

Concurrent Cell Collection and Enrichment of Target Cells for Off-Line Use Including Modification or for Discarding FIG. 4 depicts at a high level a method 400 of concurrent cell collection 410 from the patient 450, target cell enrichment 420 and return of non-target cells 452 (all depicted within circle 402). The enriched target cells 430 may be used off-line for research/testing 462, 470 or discarded 482. Alternatively, the enriched target cells 430, 462 are modified for infusion 464 of the target cells to the patient 450 at a later time. This aspect encompasses concurrent cell collection 410, target cell enrichment 420 and return 452 of non-target cells to the patient 450 in a closed loop. The leukapheresis collection step 410 yields a mononuclear cell population. An online enrichment step 420 of target cells is performed. The non-target cells are returned 452 to the patient 450. The enriched target cells 430 may be used off-line and may optionally be modified for research, testing etc 470 or infusion 464 of the target cells to the patient 450 at a later time. The target cells 462 may be used with or without modification. The cells may also be discarded 482. In the situation where target cells are modified and returned 464 to the patient, non-target cells 452 may not necessarily be given back to the patient 450. The process 400 of concurrent cell collection 410, target cell enrichment 420 and off-line cell modification may be repeated as many times as necessary, for example, to reach a certain number of target cells. Target cell enrichment 420 may be for one or several cell types. Target cell modification may be for one or several cell types. The closed loop is connected to the patient 450 at the times of cell collection 410 and cell return 452.

Figure 5:
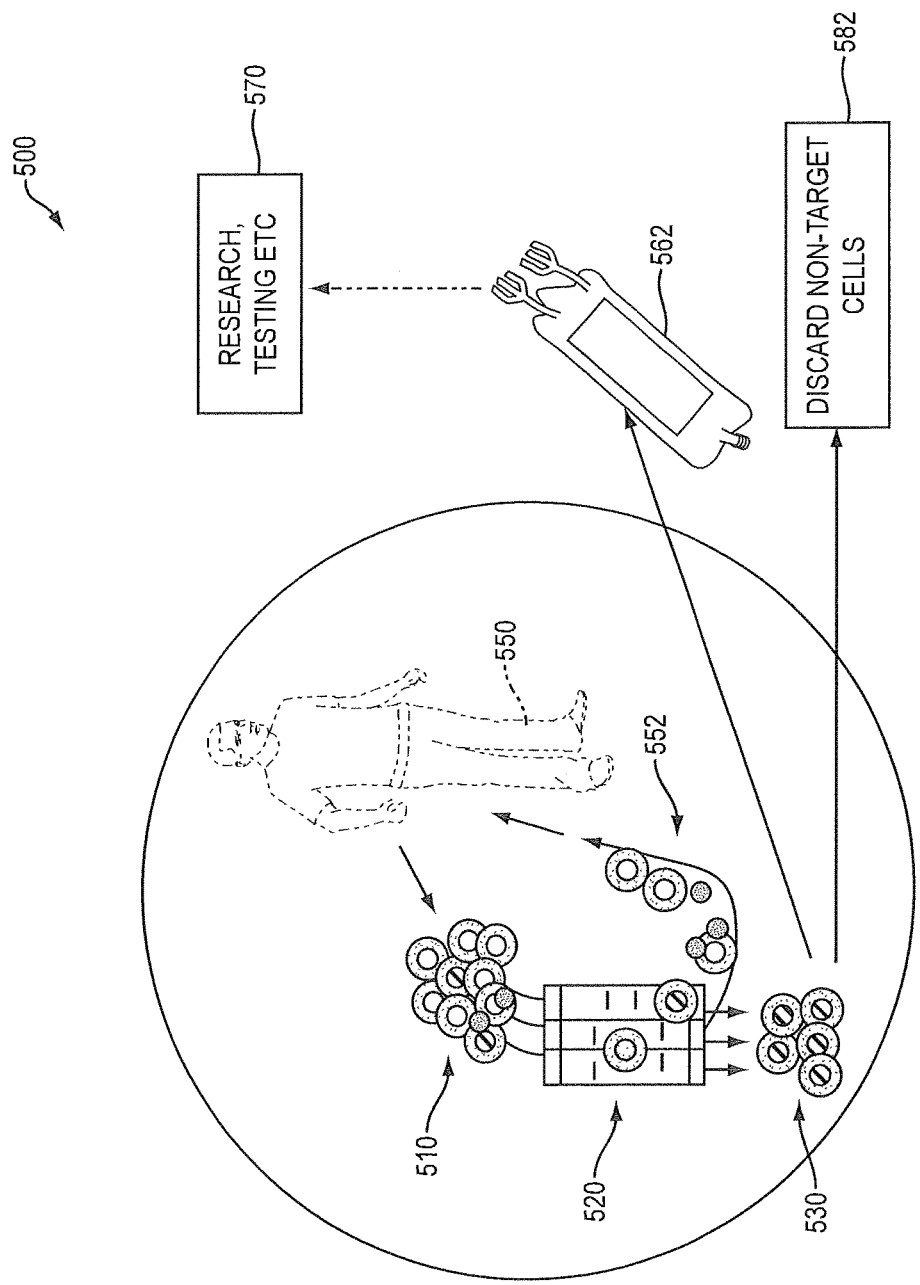
FIG. 5 is a schematic diagram depicting concurrent cell collection, target cell enrichment and return of target cells.

Concurrent Cell Collection and Enrichment of Target Cells for Return with Non-Target Cells Used Off-Line or Discarded FIG. 5 depicts at a high level a method 500 of concurrent cell collection 510 from a patient 550, target cell enrichment 520 and return of target cells 552 to the patient 550. The enriched non-target cells 530 are then used off line with or without modification for research/testing 562, 570 or are discarded 582. Again, the leukapheresis collection step 510 yields a mononuclear cell population. The online enrichment step 520 of target cells is performed. The target cells 552 are returned to the patient 550. This aspect encompasses concurrent cell collection 510, enrichment 520 of target cells and return 552 of target cells to the patient 550. Non-target cells 562 may be used off-line for research, testing etc 570 (either with or without a modification step) or are discarded 582. The closed loop is connected to the patient 550 at the times of cell collection 510 and cell return 552.

Concurrent Cell Collection, Enrichment and Modification of Target Cells

Figure 6:
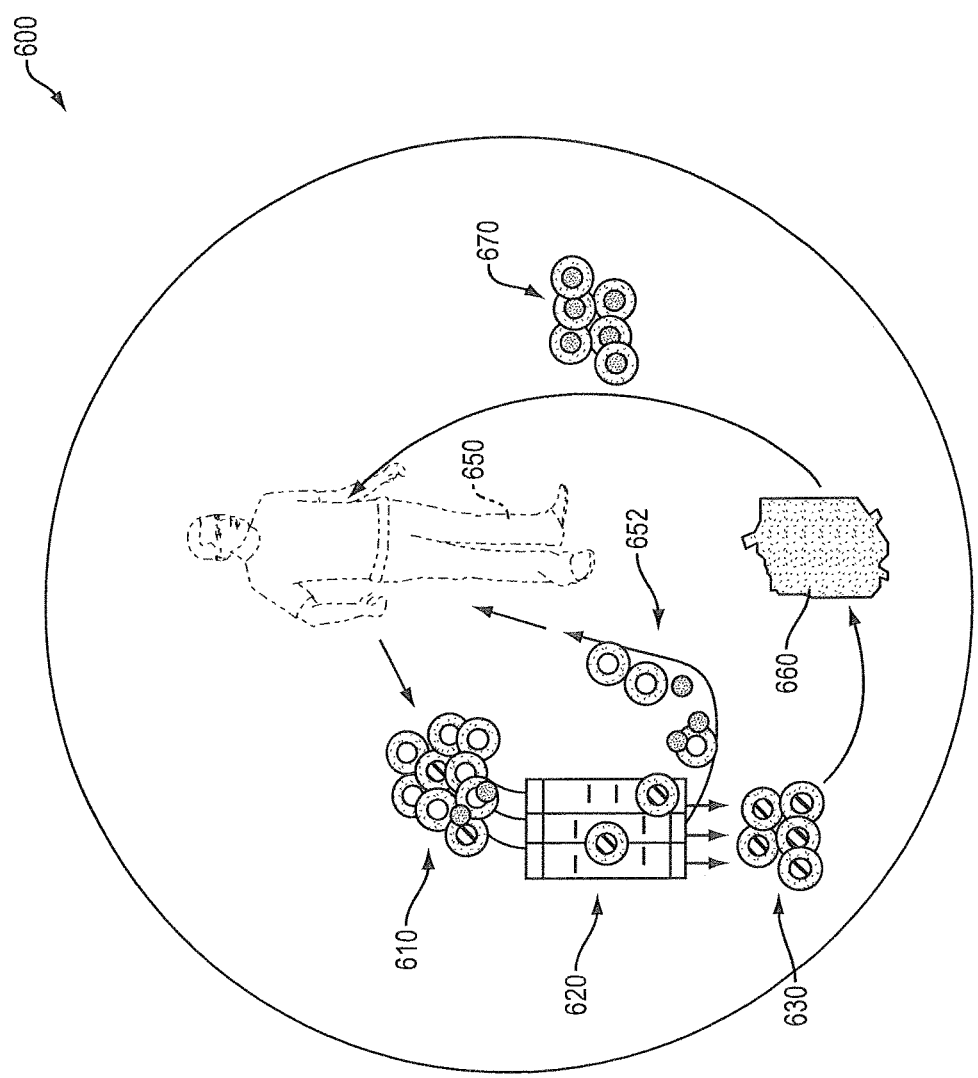
FIG. 6 is a schematic diagram depicting a method of concurrent cell collection from a patient, enrichment of target cells, modification of target cells, and return of modified target cells to the patient.

FIG. 6 depicts at a high level a method 600 of concurrent cell collection 610 from a patient 650, enrichment 620 of target cells, modification 660 of target cells 630, and return of modified target cells 670 to the patient 650. Non-target cells 652 may also be returned to the patient 650. This aspect encompasses concurrent cell collection 610, enrichment 620 of target cells, modification 660 of target cells and return of modified target cells 670 to the patient 650 in a closed loop procedure. Non-target cells 652 may optionally be returned to the patient. The closed loop is connected to the patient 650 at the times of cell collection 610 and cell return 652, 670.

Cell Collection

An embodiment of the invention comprises cell collection and concurrent cell enrichment. Collection is the leukapheresis collection of the bulk mononuclear blood cells, the cells from which the target blood cells are enriched. This step can employ any method known in the art for obtaining mononuclear cells from a patient including, without limitation, the use of differential centrifugation. Devices for this purpose include the COBE® Spectra, Trima Spectra Optia systems (all marketed by Gambro BCT) and the Amicus or CS-300 (marketed by Fenwal/Baxter) Gambro Cobe Spectra or Optia, Fenwal Amicus or CS-3000. Preferably, the differential centrifugation is conducted by a continuous flow system. In a preferred embodiment, this bulk blood cell collection uses the Therakos CellEx technology due to its superior collection efficiency and low extracorporeal volume compared to other devices, which includes such devices as listed above. During leukapheresis, the non mononuclear cell population is reinfused to the individual.

Figure 9:
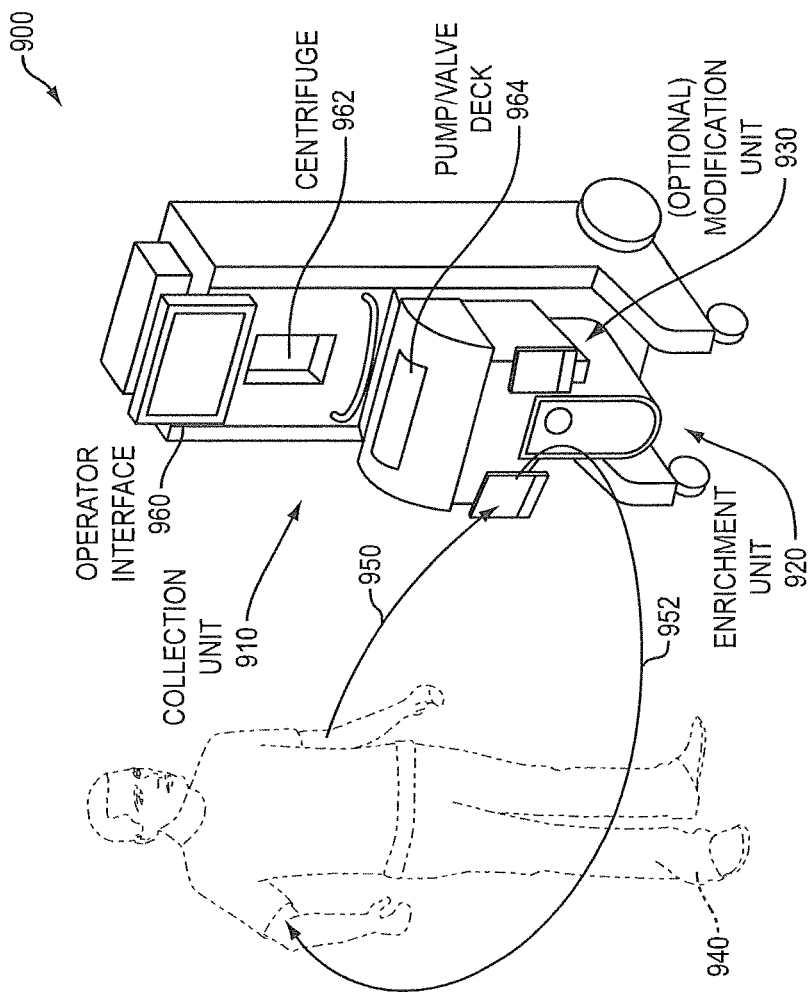
FIG. 9 is a perspective view of elements of the blood-processing device comprising the collection, enrichment and (optional) modification units or modules.

FIG. 9 illustrates the blood processing device in accordance with an embodiment of the invention. The patient 940 is coupled to the device 900 in a closed loop fashion with an input catheter 950 coupled to the patient 950 to provide blood as input to the device 900 and an output catheter 952 as a return path from the device 900 to the patient. The device 900 has an inlet interface to receive blood directly from the circulation of the patient. The device 900 also has an outlet interface to return enriched target and/or non-target cells to the circulation of the patient. The device 900 and the patient form a closed loop when coupled together. The device 900 includes a leukapheresis collection unit 910 and an enrichment unit 920. The (leukapheresis) collection unit or module 910 collects bulk mononuclear blood cells from the received blood. The enrichment unit or module 920 enrichs concurrently target cells separated from non-target cells in the bulk mononuclear blood cells. The device 900 has an operator interface 960 for receiving inputs and providing outputs to an operator (not shown). The device 900 also comprises a pump/valve deck 964. The device 900 may also comprise an optional modification unit 930. The device 900 comprises a centrifuge 962 for processing blood cells as explained hereinafter. A controller (not shown) is coupled to the operator interface 960 and the other modules for automated control of operation of the device 900

In the Therakos CellEx system, a centrifuge bowl, such as, for example, a Latham bowl, as shown in U.S. Pat. No. 4,303,193 issued to Latham, Jr on 1 Dec. 1981 and entitled "Apparatus for separating blood, into components thereof", which is incorporated herein by reference in its entirety, separates blood into red blood cells and "buffy coat". The Latham bowl is a blood component separator that has been used for some time in the medical leukapheresis market as well as in medical therapies such as extracorporeal photopheresis (ECP). U.S. Pat. No. 5,984,887 "Photopheresis treatment of leukocyte" provides descriptions of extracorporeal photopheresis and its method of cell separation and centrifugation.

Figure 7:
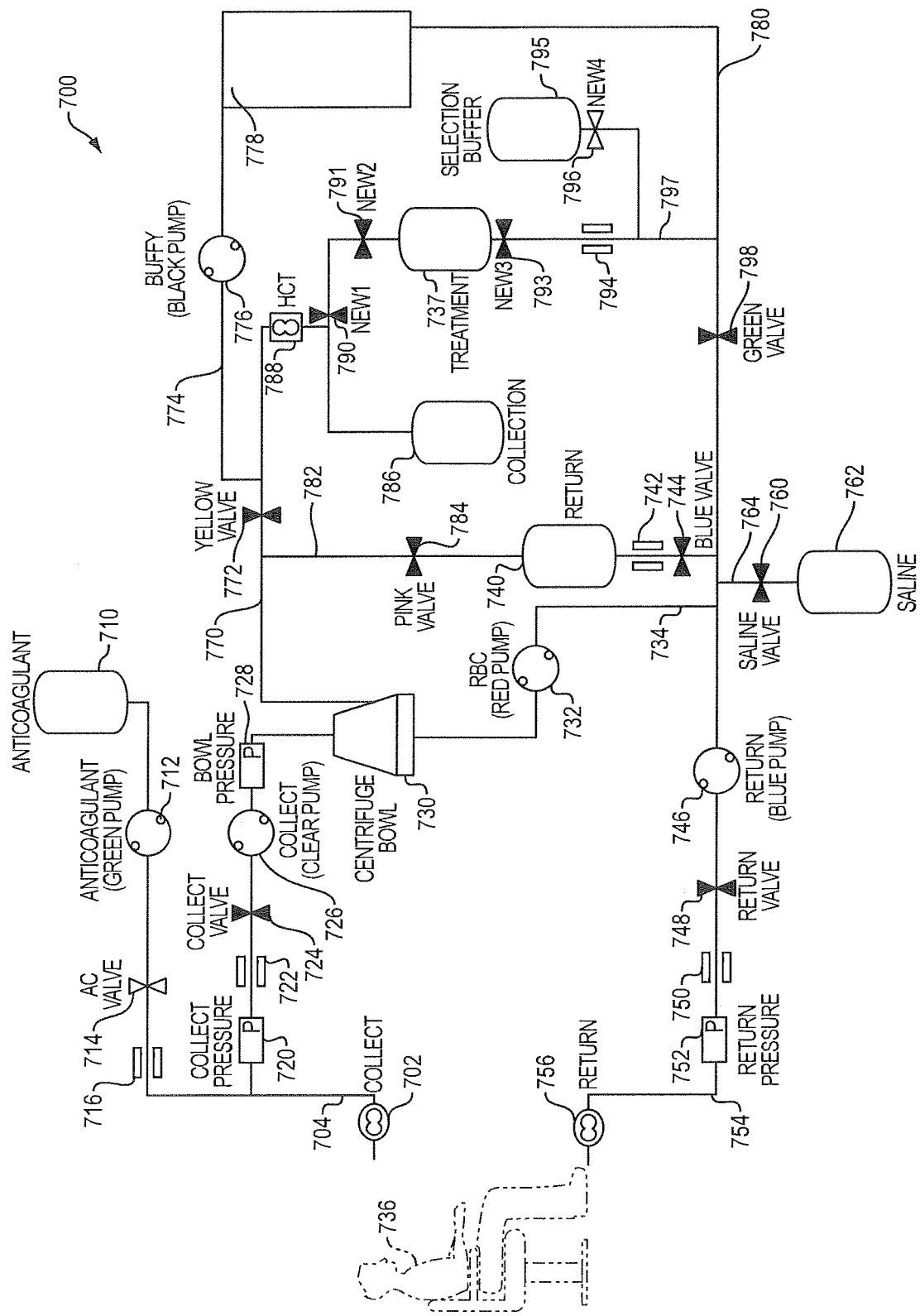
FIG. 7 is a schematic diagram of a device performing collection and enrichment in accordance with an embodiment of the present invention; Symbols present the following components: Saline bag, ; peristaltic pump, ; clamp, ; air detector, ; pressure gauge, ; clamp, 

FIG. 7 is a more detailed schematic diagram of the blood-processing device depicted in FIG. 9 (as well as the system of FIG. 10 described hereinafter). The blood-processing device 700 is shown coupled to a patient 736 in FIG. 7. A collection node 702 and a return node 756 are connected to the patient in the manner shown in FIG. 9. The collection node 702 is part of an input interface including a catheter 704, which is in turn connected to a pressure ("collect") sensor 720. In sequence, the collect pressure sensor 720 is coupled to an air detector 722, which is coupled to a collect valve 724. The collect valve 724 is coupled to a "collect" peristaltic pump 726, which in turn is coupled to the bowl pressure sensor 728. The pressure sensor 720 affects operation of the collect pump 726. The bowl pressure sensor 728 is coupled to the centrifuge bowl 730. One output of the centrifuge bowl 730 is coupled to a red blood cell pump (RBC) 732 and catheter 734, which is in turn coupled to a return path, described in greater detail hereinafter An anticoagulant (AC) bag 710 is coupled to an anticoagulant peristaltic pump 712 and appropriate catheter. The pump 712 is in turn coupled to a valve 714, which in turn is coupled to an air detector 716. The air detector 716 is coupled by a suitable catheter to the input catheter 704 and collect pressure sensor 720. This arrangement allows anticoagulant to be applied to blood input to the device 700 from the patient 736.

Another catheter 770 provides an output from the centrifuge bowl 730 and is coupled to a valve 772. Also coupled to the catheter 770 is a catheter 782 coupled to a valve 784. In turn the valve 784 is coupled to a return bag 740. The return bag 740 is coupled to an air detector 742, which in turn is coupled to a valve 744. The valve 744 is in turn coupled to a valve 798, a saline valve 760, which is in turn coupled to a saline bag 762, catheter 734 and a return pump 746. The return bag 740, air detector 742, valve 744 form a return path with the return pump 746. The pump 746 is coupled to the return valve 748, which is coupled to an air detector 750. The air detector 750 is coupled to the return pressure sensor 752, which is coupled to catheter 754 and return node 756.

The valve 772 is coupled to a sensor 788 capable of detecting red blood cells. A catheter 774 is also coupled to the valve 772 and in turn is connected to a buffy pump 776. The buffy pump 776 is coupled to a plate 778. The output of plate 778 is coupled to a catheter 797, which in turn is coupled to valve 798. Valve 798 is coupled to return pump 746. The HCT sensor 788 is coupled to parallel-configured valves 790 and 791. The valve 790 is coupled to a collection bag 786. The valve 791 is coupled to treatment bag 737 where agents for enrichment are added. The treatment bag 737 is coupled to valve 793, which in turn is coupled to air detector 794. The air detector 794 is coupled to valve 798.

A selection buffer bag 795 is coupled to a valve 796, which in turn is coupled to air detector 794.

Cell Enrichment

Figure 10:
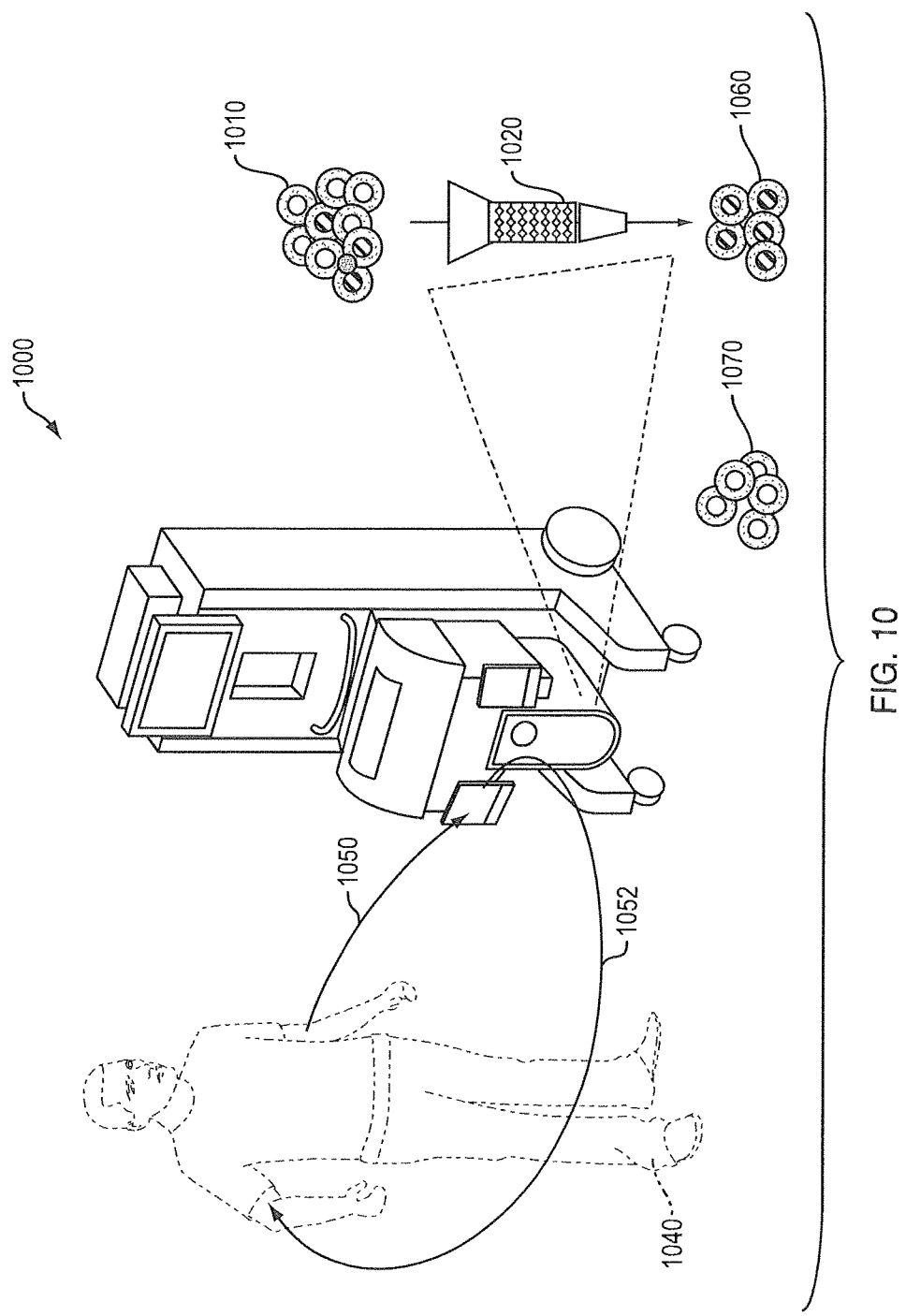
FIG. 10 is a perspective view of elements of the blood processing device, per the device of FIG. 9, but highlighting the cell enrichment module/process.

FIG. 10 shows the device 900 of FIG. 9 renumbered as device 1000. The patient 1040 is coupled with the device 1000 in a closed loop fashion with input catheter 1050 and output catheter 1052. In this embodiment the mononuclear cell population 1010 is subject to enrichment 1020, e.g. by antibody coated particle capture, such as magnetic particle capture. The output of enrichment 1020 is the enriched target cells 1060, which can be returned to the patient. Also remaining non-target cells from the enrichment 1020 may be returned to the patient 1040 via the device 1000. Cells are enriched for specific purposes, which include but are not limited to:

1. Elimination from the blood stream (eg leukemic lymphoma, myeloma cells); these cell types would be selected as cells to be eliminated from the blood and discarded.

2. Modification to give back to the patient for positive benefit; some examples include:

a. eliciting an immune response by enrichment and modification of leukemic cells or metastatic cancer cells;

b. modification to generate cytotoxic T lymphocytes targeted to a specific cancer; and c. modification of HSC/HPC to contain a gene to impact on a disease process, eg an anti-HIV gene to impact on HIV/AIDS.

3. Use for research or testing etc, which may include an optional modification step.

Target cells are cells that are enriched from peripheral blood post bulk mononuclear cell collection. Cell types that can be enriched from the leukapheresis bulk product include but are not limited B lymphocytes, T lymphocytes, CD4 and CD8 T lymphocytes, dendritic cells, monocytes, natural killer (NK) cells, T-regulatory cells, T-helper cells, cytotoxic T lymphocytes (CTLs), hematopoietic stem cells (HSCs), hematopoietic progenitor cells, endothelial cells, epithelial cells, lymphokine-activated killer cells (LAKs), tumor infiltrating lymphocytes (TILs), mesenchymal stem cells and epithelial cells—see Table 1 (Fundamental Immunology By William E. Paul 2003 Lippincott Williams & Wilkins ISBN 0781735149; Essential Haematology, Hoffbrand, Pettit and Moss).

TABLE 1

Cell Types That Can be Isolated From Peripheral Blood (with known surface markers)

Hematopoietic Progenitor Cells (CD34$^+$, CD135$^+$)
Endothelial Progenitor Cells (CD34$^+$, Flk-1$^+$, VEGRF-3$^+$, CD133$^+$)
Bone Marrow Stromal Cells
Skeletal Muscle Progenitor Cells
Cardiac Muscle Progenitor Cells
Hepatic Progenitor Cells (C1qR$_p^+$ or CD34$^+$, CD38$^+$, CD45$^+$)
Mesenchymal Stem Cells (CD29$^+$, CD44$^+$, SH2$^+$, SH3$^+$, and SH4$^+$)
Erythrocytes (CD44, Glycophorin A)
Dendritic Cells (CD11c$^+$, CD123$^+$)
T cells (CD3$^+$, CD4$^+$, CD8$^+$, CD28$^+$)
NK Cells (CD16$^+$, CD57$^+$, CD94$^+$, CD96$^+$, CD122$^+$)
B Cells (CD19$^+$, CD22$^+$, CD40$^+$, CD72$^+$, CD79$^+$)
Neutrophils (CD15$^+$, CD128$^+$)
Eosinophils (CD116$^+$, CD125$^+$)
Basophils (CD125$^+$)
Monocytes-Macrophages (CD14$^+$, CD64$^+$, CD68$^+$, CD98$^+$, CD115$^+$, CD163$^+$, Flt-1$^+$)
Megakaryocyte/Platelets (CD41$^+$, CD42$^+$, CD61$^+$, CD109$^+$)
Mast Cells (Fc.epsilon.RI.chi.$^+$)
Osteoblast Progenitors*
Osteoclasts*

*Isolated from peripheral blood but no cell surface markers identified to date.

Other cell types targeted for discarding can be any known in the art, including, without limitation cancer/leukemia cells from blood or other tissues, viral or bacterially infected cells, viruses or bacteria or parasites, fetal cells, or pathogenic effector cells. These cells can be enriched by the use of appropriate surface antigens. These latter cells can also be targeted for modification as per purpose #2 above, ie modification of cells and giving the modified cells back to effect a therapeutic immune response.

During the enrichment step, more than one target cell type may be enriched. The system may enrich multiple cell types in various ways, eg the cell types may be enriched separately in different chambers of the device (900, 1000 of FIGS. 9 and 10). The different cell types may be managed together (eg all returned or discarded or modified) or the cell types may be managed separately (eg one set returned, one set discarded, one set modified or all sets modified but in different ways) or variations of the preceding.

The enrichment of the target cell(s) may be to eliminate the target cell from the peripheral blood (as in leukemia cells) or to enrich to a percentage purity required for the therapeutic application or for research/testing etc.

Enrichment of the target cell may be by chemical or physical means, eg capture, and the target cells are said for example, to be isolated, that is enriched from the bulk blood cell population.

The enrichment procedure may employ one or more methods known in the art including, without limitation, antigen capture, beads, magnetics, fluorescent-activated cell sorting, microfluidics, solid support, acoustics, bioluminescence, antibody tagging, or enzyme substrate. Suitable solid supports include particles including, without limitation, ferromagnetic and density modified particles. These can be obtained, for instance from Miltenyi Biotec and Dynal (Curr Opin Immunol. 1991 April; 3(2):238-241). There exist methods that can be used for the release of the captured cells that include: i) competition with excess ligand, ii) enzymatic digestion, iii) change in pH, iv) change in ionic strength, v) removal of magnetic field, vi) physical agitation.

The ligand/s specific for the target cell population or populations can be any known in the art and is preferably an antibody specific for a cell surface ligand. The cell surface ligand can be a cluster designation (CD) antigen including, without limitation, CD1a, CD4, CD8, CD14, CD25, CD34 and CD133, which usually utilizes a specific antibody to capture/select the target cell. The cell surface ligand can be, without limitation EpCAM (epithelial cell adhesion molecule), selectins, adhesion molecule receptor, homing receptors, cytokine receptors, chemokine receptors and enzymes including aldehyde dehydrogenase and other intracellular enzymes. Various surface markers are indicated in Table 1.

As one example, one way of enriching cells is the use of antibodies or aptamers. The term antibody refers to an immunoglobulin molecule capable of binding an epitope present on an antigen. As used herein, the term antibody refers to cell-binding molecules. The term is intended to encompasses not only intact immunoglobulin molecules such as monoclonal and polyclonal antibodies, but also bi-specific antibodies, humanized antibodies, chimeric antibodies, anti-idiopathic (anti-ID) antibodies, single-chain antibodies, Fab fragments, F(ab') fragments, fusion proteins and any modifications of the foregoing that comprise a ligand recognition site of the required specificity. As used herein, an aptamer is a non-naturally occurring nucleic acid or peptide having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule.

HSC/HPC can be enriched by a variety of methods including use of the cell surface markers CD34 or CD133 or elevated levels of alcohol dehydrogenase (ALDH). In one embodiment of the present invention, CD34+ HSC/HPC cells are enriched and then modified by the step of introduction of an anti-HIV gene. This introduction may be performed by a variety of means eg by retroviral transduction.

Target cells may be returned to the patient. In certain medical conditions, it may be advantageous to either discard or retain for diagnostic/monitoring purposes the targeted cell populations. For instance in the diagnostic procedure developed by Immunicon Inc. termed CellSearch™ rare tumor cells are measured in blood by a magnetic bead separation system (reference). This larger scale collection procedure could increase sensitivity of such a diagnostic method. Discarding of specific target tumor cells or pathogenic cells such as Th17 cells in autoimmune disease could be beneficial (reference). Finally, lymphopenia induction has been associated with better outcome to certain therapies for reasons such as providing space for cell therapy (Dudley, M E et. al. Science. 2002 Oct. 25; 298(5594):850-4. Epub 2002 Sep. 19). Cell populations targeted for discarding can be any known in the art, including, without limitation malignant cells from blood or other tissues, viral or bacterially infected cells, viruses or bacteria or parasites, fetal cells, or pathogenic effector cells such as Th1, Th17, CTL, etc. This enrichment is conducted and the percent purity required for the therapeutic application is achieved. In certain cases a specific percentage enrichment is required (see below). In the case of removing pathogenic cells, for instance cancer/leukemia cells, the efficiency of clearance from the blood is more important than the actual final percent purity. These cells can also be targeted for modification as per purpose #2 above.

The two steps of cell collection and enrichment are performed in a closed-loop manner in a single device; the steps can be performed in the same or different sections of the device. The non-target cells may be returned to the patient or discarded, as therapeutically required, or used off-line for research/testing. In the case of immune compromised or lymphopenic conditions such as HIV, for instance, non-target cells can be returned in the closed-loop system allowing for the return of essential cells, the loss of which might compromise the patient. In other cases where the non-target cells are not required to be returned or there would be benefit from the non-target cells not being returned the non-target cells can be discarded or used off-line for other purposes. Such benefit may arise as a result, for instance, of making the patient lymphopenic that can enhance the efficacy of certain cell therapies. (Dudley, M E et. al. Science. 2002 Oct. 25; 298(5594):850-4. Epub 2002 Sep. 19).

Cell Modification

Figure 11:
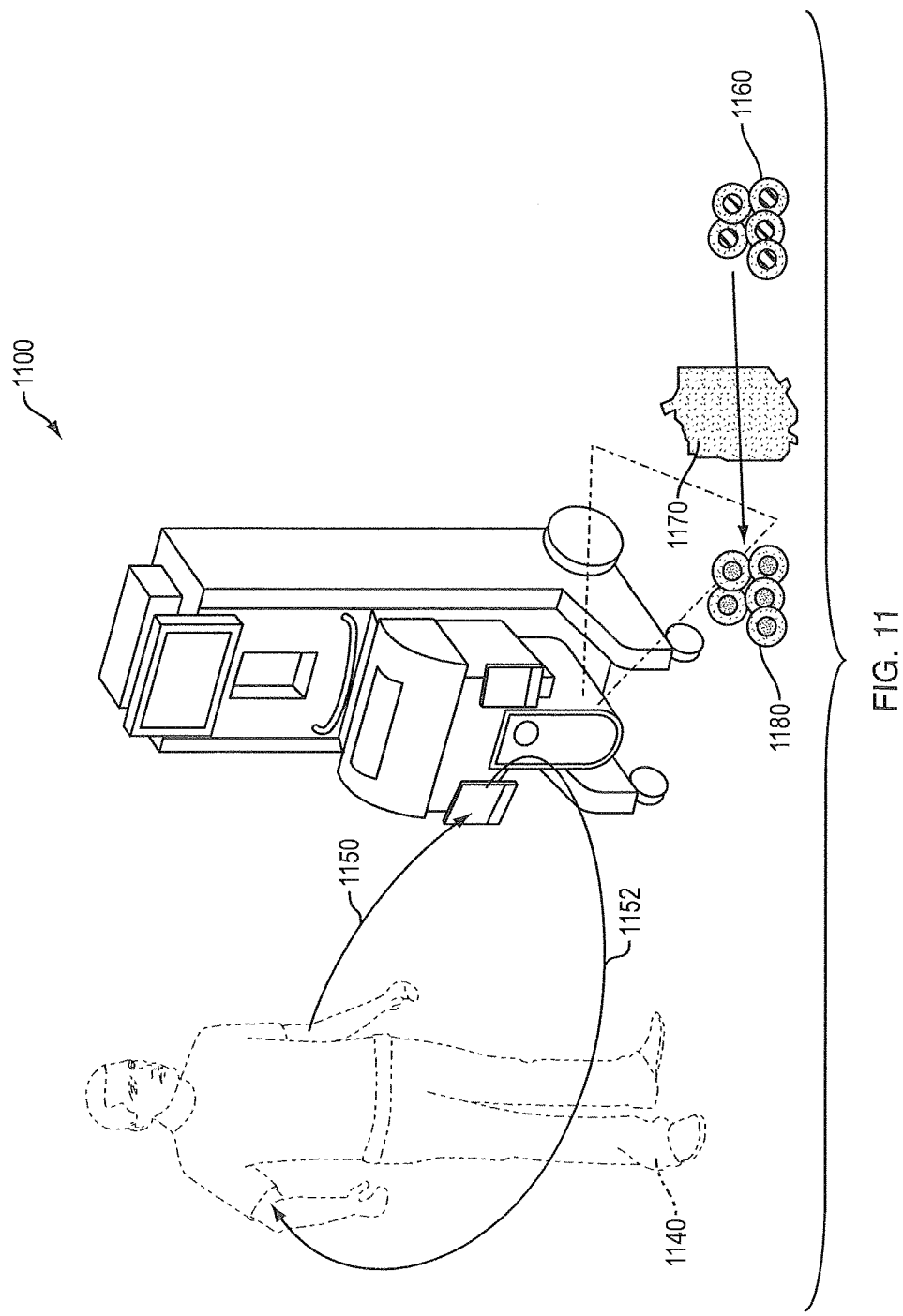
FIG. 11 is a perspective view of elements of the blood processing device, per the device of FIG. 9 or 10, but highlighting the optional cell modification step within the device.

FIG. 11 shows the device 900 or 1000 of FIG. 9 or 10 renumbered as device 1100. The patient 1140 is coupled with the device 1100 in a closed loop fashion with input catheter 1150 and output catheter 1152. In this embodiment, there is provided an additional modification step of the target cells in a closed-loop patient-connected manner. This step represents an extension of the patient-connected closed-loop system of cell collection and enrichment. Modification of the target cells in a patient-connected closed-loop system can be performed as an extension of the patient-connected closed-loop system of collection and enrichment. As shown in FIG. 11, the enriched target cells 1160 are modified in a container 1170 to provide modified target cells 1180. The optional modification can be any one or more of electroporation, lipofection, viral transduction, light (ultraviolet A (UVA), ultraviolet B (UVB), etc), addition of drugs, cell activation, pressure, heating, etc.

Figure 8:
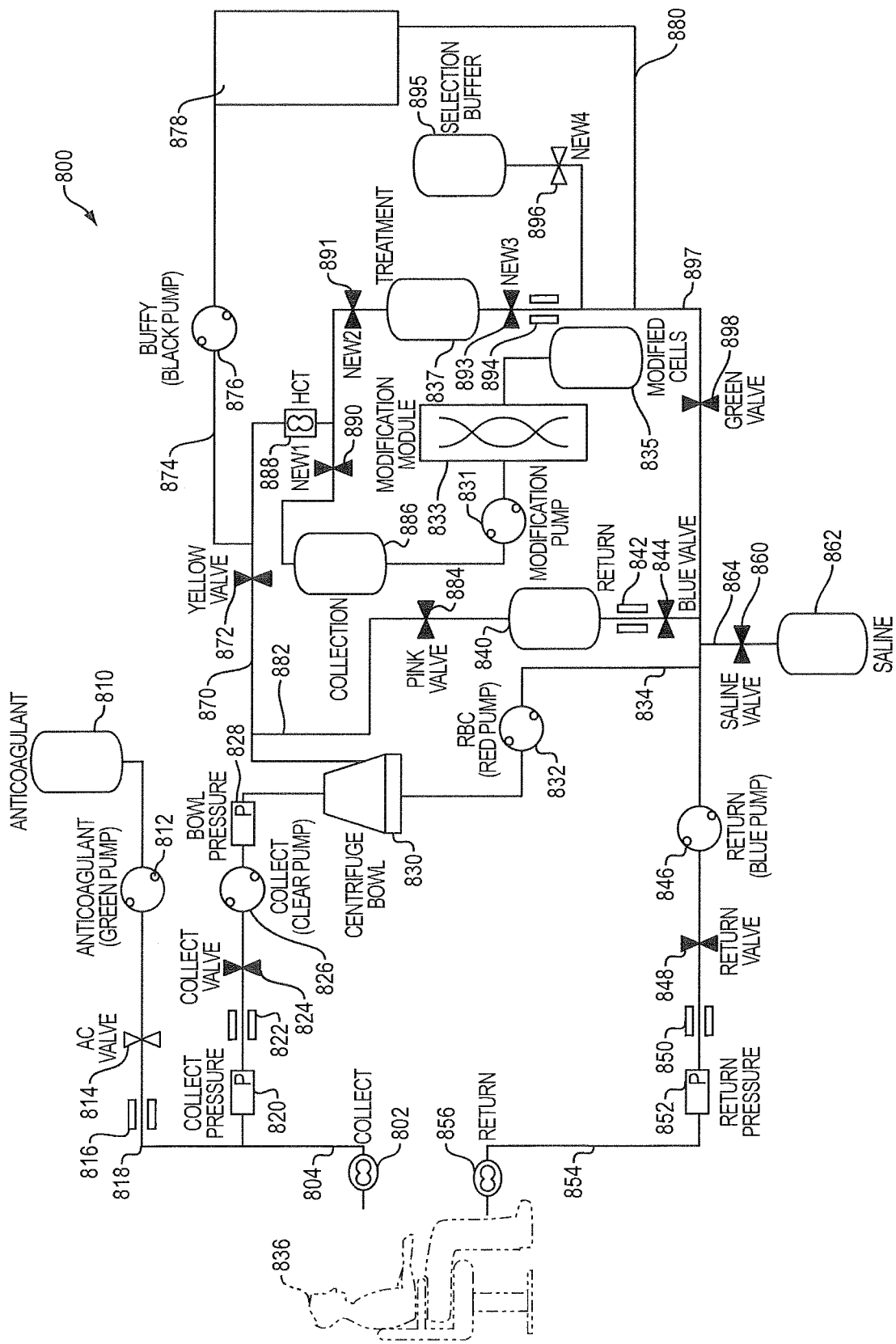
FIG. 8 is a schematic diagram of a device performing collection, enrichment, and modification in accordance with another embodiment of the present invention Symbols represent the following components: Saline bag, ; peristaltic pump, ; clamp, ; air detector, ; pressure gauge, ; clamp, 

FIG. 8 is a more detailed schematic diagram of the blood-processing device depicted in FIG. 11. The blood-processing device 800 is shown coupled to a patient 836 in FIG. 8. Elements of the device 700 shown in FIG. 7 that are the same in the device 800 of FIG. 8 have the same corresponding reference number except that the first digit is changed to correspond with the figure number (7XX and 8XX), so collect node 702 of FIG. 7 is collect node 802 of FIG. 8. For the sake of brevity only, the description of corresponding features will not be repeated in the description of FIG. 8 since those elements of FIG. 7 that are the same in FIG. 8 have the same function and configuration. Instead only the differences between FIGS. 7 and 8 are described hereinafter. The collect bag 886 is coupled to a modification pump 831, which in turn is coupled to a modification unit or module 833. The modification module 833 is in turn coupled to a modified cells bag 835. The configuration of the device 800 of FIG. 8 is otherwise the same as that of FIG. 7.

Modification may also be performed as a discontinuous ex vive cell modification to alter cell phenotype, genotype or activity. This can be by the addition of cytokines, cross linking specific receptors, addition of antigen, transfection of DNA, RNA or protein, apoptotic cell induction, gene incorporation including viral transduction. In this embodiment, the enriched target cell population 1160 is withdrawn for a separate discontinuous modification step to alter cell phenotype/genotype/activity. The modified cells can then be used for research or for therapeutic application by infusing back into a patient. The degree of enrichment is that required for research/testing purposes or for the therapeutic application.

The enriched target cell population can be modified by any method known in the art, including, without limitation, activation, expansion, induction of apoptosis, genetic manipulation, induction of antigen-specificity, etc. This can be achieved, for example, by the addition of cytokines, cross linking specific receptors, addition of antigen, introduction of DNA, RNA or protein, viral transduction, electroporation, lipofection, treatment with various wavelengths of light, addition of drugs, capture of cells or cell components, pressure, heating, etc.

Cells can be modified by a variety of means that are in all cases but the one of photopheresis (see below), conducted in a patient-disconnected process by a stand-alone process or device. There are many present examples of patient-disconnected procedures involving ex vive cell modification to alter cell phenotype/genotype/activity; this can be for example by the addition of cytokines, cross linking specific receptors, addition of antigen, transfection of DNA or RNA, introduction of protein, apoptotic cell induction, or gene incorporation by for example viral transduction. The means to do this include but are not limited to electroporation, lipofection, viral transduction, irradiation, incubation with drugs, cell capture, cell activation, pressure, heating, cross-linking cell surface receptors, treatment with cytokines, chemokines, hormones, etc. For example, electroporation, or electropermeabilization, is a method used to introduce extracellular compounds such as genetic material (DNA or RNA) into a cell by increasing permeability of the cell membrane caused by an externally applied electrical field. This technique is now used routinely for research purposes and clinical trials have now been conducted showing its potential utility in human therapy.

Cells targeted for modification include but are not limited to B lymphocytes, T lymphocytes, CD4 and CD8 T lymphocytes, dendritic cells, monocytes, natural killer (NK) cells, T regulatory cells, T-helper cells, cytotoxic T lymphocytes (CTLs), hematopoietic stem cells (HSCs), hematopoietic progenitor cells, endothelial cells, epithelial cells, lymphokine-activated killer cells (LAKs), tumor infiltrating lymphocytes (TILs), and epithelial cells—see Table 1. (Fundamental Immunology by William E. Paul 2003 Lippincott Williams & Wilkins ISBN 0781735149; Essential Haematology, Hoffbrand, Pettit and Moss).

These modified cells are useful for treatment of a variety of diseases and conditions. For example, adoptive T cell therapy is described by C. H. June. J. Clin. Invest. 117, (2007) 1466-1476. In this example peripheral blood lymphocytes are collected from the patient, enriched in a separate step and incubated with activation systems to increase anti-tumor CTL activity. HSCs have been used in bone marrow transplantation for many years and are increasingly used in other applications such as cardiovascular therapy and wound healing.

Modifications can be effected using any method known in the art including, without limitation, transfection or transduction of genetic material into at least a portion of the target cell population, cross-linking specific receptors or treatment with cytokines. Transfection or transduction of genetic material can be by any method known in the art including, without limitation, by vector transduction, electroporation or lipofection. The modification can be any known in the art including, without limitation, cytotoxic T lymphocyte (CTL) activation, T regulatory cell (Treg) activation, induction of apoptosis or gene modification of blood cells for protection from human immunodeficiency virus (HIV).

Figure 2:
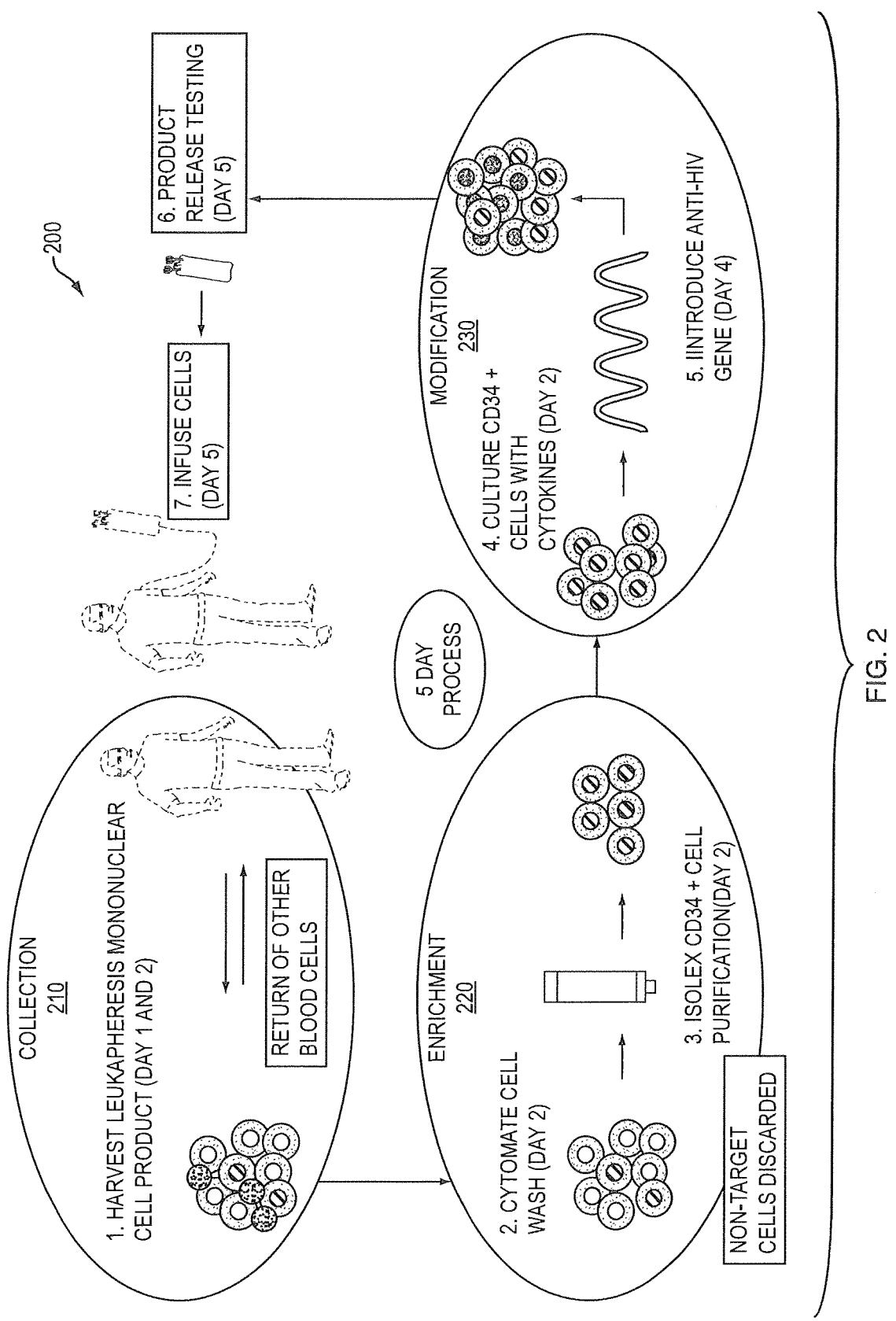
FIG. 2 is a schematic diagram depicting a specific example of a current method for cell collection, enrichment and modification.

Treatment of HIV with genetically modified hematopoietic progenitor/stem cells is described in Amado et al (2004), International (PCT) Patent Publication No. WO 03/006691. In this system, the HSC/HPC are collected from the patient as part of the mononuclear cell fraction by leukapheresis, enriched by a separate Baxter device, transduced and incubated prior to infusion to the patient (see FIG. 2). In the embodiments of the invention, patients are leukapheresed for a shorter time, the cells will be safely enriched in a closed loop, and most importantly, the non-target cells can be returned to these patients who are lymphopenic (see FIG. 4).

There are many other target cells that may be enriched by the device and used for therapy and some examples are given here. Dendritic cells are used in treating cancer, infectious diseases and immunodeficiency diseases (Nature. 2007 Sep. 27; 449(7161): 419-26. Review). NK cells are used to treat cancer. T-regulatory cells are being tested for treating graft versus host disease (GvHD) (Semin Immunol. 2006 April 18(2): 78-88), immunodeficiency diseases, atopic dermatitis and asthma (Curr Opin Allergy Clin Immunol. 2006 February; 6(1):12-6. Review). CTLs are used in treating cancer, infectious diseases and allergies. Endothelial cells are used in cellular regeneration therapies of bladder, vasculature, etc.

In an embodiment combining all three steps of collection, enrichment and modification in a patient-connected closed-loop, the degree of enrichment and modification are determined by the values required for the therapeutic application. For example, in HIV gene therapy enrichment of the HSC/HPC to >20% is required and more preferably >80/o so that a high number of HSC/HPC can be transduced with the anti-HIV gene construct. Transduction needs to be optimized so that a high number of gene-modified HSC/HPC are re-infused to the patient. The foregoing is provided by way of example only.

In another example, T-regulatory cells can be enriched and then expanded; the purity generally required is >75% and preferably >90% to limit the outgrowth of effector T cells during the modification/stimulation step. Thus, the enrichment and modification parameters vary by disease and medical need. Again, the foregoing is provided by way of example only.

In a further embodiment, the embodiments of the invention allow for monitoring the steps as the steps occur, that is, in real time such as the measurement of hematocrit, cell number, cell phenotype, cell activation, cell size, etc. In the case of, for instance, HSC/HPC enrichment & modification, this allows for determination of parameters of the process as it is occurring e.g. measurement of the number of CD34+ cells and the number of transduced CD34+ cells.

All references cited herein are hereby incorporated by reference. These include U.S. Pat. No. 7,211,037 ("Apparatus for the continuous separation of biological fluids into components and methods of using same") issued to Briggs, et al. on 1 May 2007 and U.S. Pat. No. 7,186,230 ("Method and apparatus for the continuous separation of biological fluids into components") issued to Briggs, et al. on 6 Mar. 2007. The following example is provided to illustrate, but not limit, the embodiments of the invention.

EXAMPLE 1

Collection of Mononuclear Cells from Peripheral Blood and Enrichment of CD4+ T-Lymphocytes A peripheral blood bag was prepared to represent a faux patient. Four (4) units of ABO matched whole blood from healthy donors was collected into ACD-A anticoagulant, 1-2 days prior to use. The units of blood were white blood cell depleted by filtration through a Sepacell leukoreduction filter and pooled into a 2 L blood bag. A leukopak buffy coat was added, to bring the white cell count to physiological concentrations and the faux patient bag was maintained at room temperature on a rocking platform to ensure a homogeneous cell suspension. A 10 mL sample was withdrawn from the faux patient bag and baseline cell composition was determined by electronic cell count and automated differential on a Beckman Coulter AcT counter, and immunophenotype was evaluated by flow cytometry using a panel of monoclonal antibodies including CD45-FITC, CD3-PECy7, CD4-APC, CD8-PECy5, CD14-PECy7, CD15-PE, CD20-APC, CD34-PE.

An example of the cell composition within a faux patient bag is:

|  | Faux patient Whole Blood |
|---|---|
| Cell Counts | |
| WBX (×10^6) | 5.1 |
| Lymphocytes | 1.85 |
| Monocytes | 0.4 |
| Neutrophils | 2.85 |
| RBC | 4.35 |
| Platelets | 85.5 |
| Hemoglobin | 11.4 |
| Hct (%) | 35.8 |
| Immunophenotype | |
| CD8 (%) | 6.5 |
| CD4 (%) | 25.9 |
| CD14 (%) | 12.3 |
| CD15 (%) | 57.7 |
| CD20 (%) | 2.3 |

Blood Processing System

The Therakos CellEx Photopheresis System formed the basis of the blood-processing device. As depicted in FIG. 9, the system 900 comprises several components including a centrifuge chamber 962, a pump deck 964, a photoactivation chamber, and a user-friendly software driven operator interface 960. Additional clamps and pumps are added as required and a CellEx Photopheresis procedure specific single-use disposable set was modified for use in this example. In the present example of collection of mononuclear cells and enrichment of CD4+ cells from peripheral blood, the photoactivation chamber is not required. The CellEx Photopheresis System uses a one-omega two-omega centrifugation technology that, in combination with a Latham bowl coupled to a three-port lumen drive tube, allows for continuous whole blood processing. Compared to other leukapheresis devices, collection of a similar number of mononuclear cells can be achieved from a reduced extracorporeal volume. The CellEx Photopheresis System can be operated in single (batch return) or double needle (continuous return) mode of access, which provides flexibility for the patient. In the present example, double needle mode was employed for single pass of blood from the faux patient bag to the faux patient return bag.

Prior to collection of mononuclear cells, the Therakos CellEx Photopheresis System requires the loading and priming of a disposable procedural kit. The kit was a single-use, integral, disposable set comprised of several elements including a Latham centrifuge bowl, a pump tubing organizer, and a photoactivation module. In this example, the procedural kit was modified to include additional bags and clamps. The modified, procedural kit was installed and primed as per the Therakos CellEx Photopheresis System Operators Manual. Once the kit was loaded, the system performed an automated seven-minute priming procedure to ensure proper kit loading, to test kit integrity and to test instrument integrity, as well as prime the sterile fluid pathway with anticoagulant. The anticoagulant used in this example was ACD-A.

Following priming, the system was ready for faux patient connection. The 2 L faux patient blood bag was connected to the inlet or 'kit collect access' line of the CellEx System disposable kit. An empty 2 L blood bag was connected to the outlet or 'kit return access' line to represent the other arm of the faux patient and designated as the "return bag". Following connection of the two donor access lines, the CellEx System was configured to operate in double needle mode. All other system parameters were used at the default settings. The system parameters were:

1) process 1500 mL whole blood,
2) blood collection rate of 50 mL/min, and
3) anticoagulant ratio of 10:1.

Blood collection was initiated by pressing the start button on the operator interface and the system automatically processed the targeted whole blood volume of 1500 mL.

As blood was continuously pumped from the faux patient into the Latham bowl, red blood cells and plasma were continuously removed and returned via a second intravenous line represented in this example by the "return bag". In single needle mode, the red cells and plasma are returned via the same line in a batch mode. The CellEx System pump deck drives multiple pumps and directs and displaces the blood components throughout blood processing. Mononuclear cells were retained as a white cell or "buffy coat" layer between the red blood cells and the plasma in the bowl. The position of the "buffy coat" was monitored by means of a laser beam.

When 1500 mL of whole blood had been processed, the CellEx System entered 'buffy coat collection' mode. Harvesting of mononuclear cells was accomplished by stopping the pump that controls flow of red blood cells to the "return bag". This allowed red blood cells to enter the bowl and to displace the "buffy coat" upwards, albeit with some disturbance of the white cell layer, and out via the plasma port at the top of the bowl through an open valve. The plasma and "buffy coat: was directed to the "treatment bag" previously primed with anticoagulant. When the system hematocrit optical sensor detected a hematocrit of 3%, the collect pump was temporarily stopped, and the bowl spun to allow the white cell band to reform. Collection into the treatment bag then proceeded until the optical sensor detected a hematocrit of 24%. This triggered the valve to close and divert the fluid from the bowl to the return line. The 'treatment bag" at this time contains the collected mononuclear cell preparation. The 'treatment bag' consisted predominantly of mononuclear cells, while also containing platelets, and a low concentration of granulocytes and red cells with a hematocrit of approximately 1-2%. The cell "treatment bag" was connected via the modified procedural set to an additional bag for the purpose of enrichment.

Example of mononuclear cell collection from 1570 mL anticoagulated whole blood (faux patient) is:

|  | Faux Patient Whole Blood Total Cells | Monomuclear Collection Total Cells | Yield (%) |
|---|---|---|---|
| Cell Counts |  |  |  |
| WBC (×10^6) | 8007 | 3757 | 47 |
| Lymphocytes (×10^6) | 2904 | 2939 | 101 |
| Monocytes (×10^6) | 628 | 343 | 55 |
| Neutrophils (×10^6) | 4475 | 486 | 109 |
| RBC (×10^9) | 6822 | 48 | 0.7 |
| Platelets (×10^6) | 134235 | 59007 | 44 |
| Hemoglobin (g/dL) | 11.35 | 0.55 |  |
| Hct (%) | 35.8 | 1.9 |  |
| Immunophenotype |  |  |  |
| CD8 (×10^6) | 520 | 575 | 110 |
| CD4 (×10^6) | 2074 | 225 | 109 |
| CD14 (×10^6) | 985 | 909 | 92.3 |
| CD15 (×10^6) | 4620 | 556 | 12.0 |
| CD20 (×10^6) | 184 | 229 | 124 |

Enrichment from Collected Mononuclear Cells of CD4+ Target Cells

On completion of the CellEx mononuclear cell collection, a fraction of the mononuclear cell product was washed with cell enrichment buffer and CD4+ selection beads (Dynal) were introduced at a concentration via the needle-free access port of the 'treatment bag'. The mononuclear cell and bead mixture was incubated for 30 minutes with recirculation through the serpentine pathway of the photoactivation module of the CellEx disposable kit. The incubation was terminated by displacing the cells via a peristaltic pump into a bag placed in a Magnetic particle concentrator. The CD4+ target cells were retained in the "enriched cell bag" and Dynabeads removed by addition of detechabeads. Both target CD4+ enriched and the non-target cell fractions were collected in separate collection bags. Samples were taken to determine cell number, yield and purity using a Coulter cell counter and flow cytometry of relevant cell surface markers.

The numbers shown below are for a small 2 mL aliquot of collected mononuclear cells.

|  | Monomuclear Collection Total Cells | Enriched Target Cells CD4 | Yield (%) |
|---|---|---|---|
| Cell Counts |  |  |  |
| WBC (×10^6) | 34 | 6.6 | 19.5 |
| Lymphocytes (×10^6) | 16.6 | 6.5 | 24.6 |
| Monocytes (×10^6) | 3.1 | 0.1 | 2.2 |
| Neutrophils (×10^6) | 4.4 | 0.01 | 0.3 |
| RBC (×10^9) | 0.43 | 0 | 0 |
| Platelets (×10^6) | 534 | 0 | 0 |
| Immunophenotype |  |  |  |
| CD8 (×10^6) | 15.3 | 2.9 |  |
| CD4 (×10^6) | 59.9 | 99.2 |  |
| CD14 (×10^6) | 24.2 | 2.5 |  |
| CD15 (×10^6) | 14.8 | 2.2 |  |
| CD20 (×10^6) | 6.1 | 2.6 |  |

EXAMPLE 2

Figure 12:
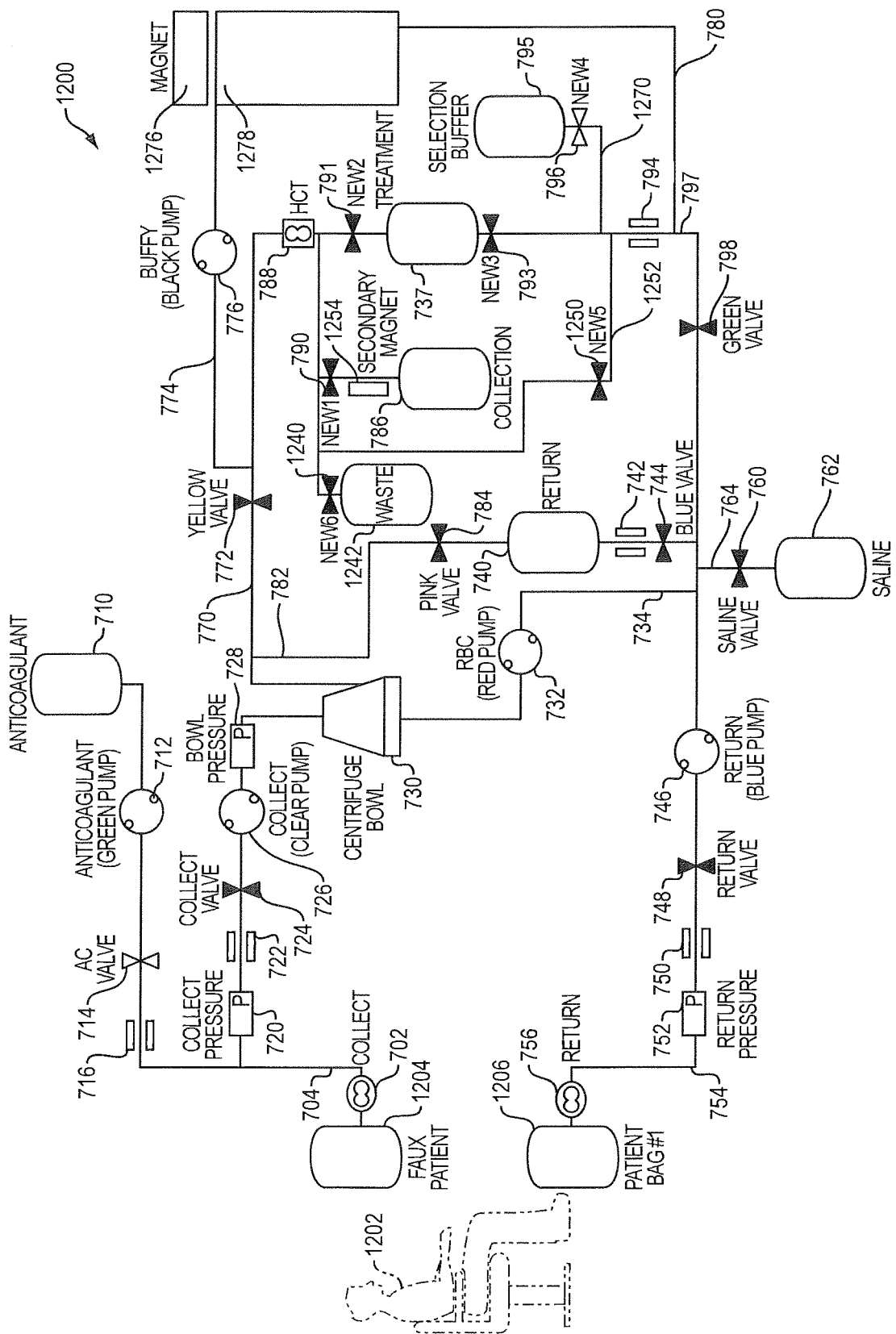
FIG. 12 is a schematic diagram of a device performing collection and enrichment in accordance with still another embodiment of the present invention. Symbols represent the following components: Saline bag, ; peristaltic pump, ; clamp, ; air detector, pressure gauge, ; clamp, ; magnet.

Collection of Mononuclear Cells and Enrichment of CD8+ Cells from Peripheral Blood Overview FIG. 12 illustrates a modified system 1200 related to the system 700 of FIG. 7. For the sake of brevity only, features of FIG. 7 that are identical in the system 1200 of FIG. 12 retain the same reference numerals (e.g., anticoagulant pump 712 in FIGS. 7 and 12). Also, these identically numbered features also retain the same configuration in the system 1200 of FIG. 12 unless described explicitly otherwise hereinafter. The system 1200 of FIG. 12 is a blood processing device that involves collection and enrichment (Version 2) and comprises 3 new bags, 6 new clamps, and 2 magnets. A standard CellEx Procedural Kit was modified as illustrated in FIG. 12. The photoactivation chamber was replaced by a CLINIcell25 bag 1278. The patient 1200 is represented in FIG. 12 by Patient Bag #1 1206 coupled to the return node 756 and by a Patient Bag #2, which is not shown in FIG. 12 but can be substituted for bag 1206 and coupled to return node 756 at different stages of the process, to allow enumeration of cells during collection and enrichment.

The system of FIG. 12 is modified as follows. A magnet 1276 is disposed adjacent the plate 778 and can be engaged and disengaged with the plate 778. In FIG. 7, the output of the HCT sensor 788 is coupled to the valves 790 and 791 (NEW1 and NEW2) in parallel, which in turn are coupled to the collection and treatment bags 786 and 737, respectively. In FIG. 12, this configuration is maintained, but additional parallel pathways are added to the output of the HCT sensor 788. A valve (NEW6) 1240 is coupled to the output of the HCT sensor 788 and in turn to a waste bag 1242. A further valve (NEW5) 1250 is coupled to the output of the HCT 788, and a catheter 1252 is coupled between the valve 1250 and the valve (NEW3) 793, and the air detector 794. Further, the output of the valve (NEW4) 796 is coupled in FIG. 12 between the valve 793 and the air detector 794, instead of between the air detector 794 and the valve 798 as shown in FIG. 7. Finally, a secondary magnet 1254 is disposed adjacent a pathway between the valve (NEW1) 790 and the collection bag 786.

Four whole blood units were combined to create a "faux-patient" 1204 coupled to collection node 702 and a sample was taken for coulter counter and flow cytometry analysis. The modified kit was loaded onto a CellEx device and valves NEW1 790, NEW4 796, NEW5 1250, and NEW6 1240 were closed and the valves NEW2 791 and NEW3 794 were opened. As an initial state, this provided an open channel for fluid communication through the treatment bag 737. The standard CellEx software was used to prime the kit, and diagnostic software running on a laptop was connected to the IR port of the CellEx to allow additional user configured operation of the pumps, valves, and centrifuge.

Priming

The valve NEW2 791 was closed and the valve NEW1 790 was opened to create a pathway to the Collection Bag 786, and this line was primed with buffer by circulating the Buffy/Recirculation Pump 776 clockwise. Once the line was primed, the pump 776 was stopped, the valve NEW3 793 was closed, and the valve NEW4 796 was opened to allow Selection Buffer 795 to be pumped throughout the kit. The Buffy/Recirculation pump 776 was activated counter-clockwise. After priming the line to the Selection Buffer 795, the pump 776 was stopped, the valve NEW 790 was closed, and the valve NEW6 1240 was opened. This opens the pathway to the Waste Bag 1242. By activating the Buffy/Recirculation Pump 776 in a clockwise direction, the line to the Waste Bag 1242 was primed. When this line to the Waste Bag 1242 was primed, the pump 776 was stopped, the valves NEW6 1240 and NEW4 796 were closed, and the valve NEW5 1252 was opened to prime the line 1252 that bypasses the Treatment Bag 737 by running the Buffy/Recirculation Pump counter-clockwise. Once the line 1252, 1250 was primed, the pump 776 was stopped, the valve NEW5 1250 was closed, and the valves NEW2 791 and NEW3 793 were opened; priming was complete.

Connection of "Patient" and Collection

The "faux-patient" 1204 was connected to the Collect line 702, 704 and the Patient Bag #1 1206 was connected to the Return line 756, 754. A standard CellEx double-needle procedure using default settings was run to collect the buffy coat (as described in Example 1 hereinbefore). Immediately following the buffy coat collection, the "Stop" button was pressed, halting the automated CellEx software. The CellEx pumps, NEW valves and centrifuge were then manipulated by the operator and with the diagnostic software on the laptop.

Enrichment of Target Cells

All valves in the system 1200 were closed except valves (NEW2) 791, (NEW4) 796, (Blue—Plasma Bottom) 744, (Pink—Plasma Top) 784, and (Return) 748. This created an open pathway for the remaining material in the bowl 730 and Return Bag 740 to be pumped to Patient Bag #1 1206. This was achieved by enabling the Red Blood Cell Pump 732 to turn clockwise and the Return Pump 746 counter-clockwise. This created a pathway from the centrifuge bowl, through pumps 732 and 746 to the patient bag #1 1206 via elements 748, 750, 752, 754, and 756 and through return bag 740. The pumps 732, 746 were stopped, the valve (Blue—Plasma Bottom) 744 was closed, and the Saline valve 764 was opened. To wash the bowl 730, the Red Cell Pump 732 was activated in a counter-clockwise direction and saline from the saline bag 762 was pumped into the bowl 730. When the bowl 730 was approximately half full, the pump 732 was stopped and the Saline valve 764 was closed. The centrifuge 730 was then pulsed, and the blood pumped to Patient Bag #1 1206 via the Red Blood Cell Pump 732 clockwise and the Return Pump 746 counter-clockwise. When the bowl 730 was empty, the Red Blood Cell Pump 732 was deactivated, and the speed of the Return Pump 746 was raised briefly to flush the remaining blood from the lines and into the Patient Bag #1 1206. The pump 746 was stopped, and the Patient Bag #1 1206 replaced with Patient Bag #2 (not shown in FIG. 12), which was coupled to return node 756. A sample from Patient Bag #1 was analysed on a coulter counter and by flow cytometry for cell composition. A total of 1800 ml of blood was processed, at a total nucleated cell count of $6.6 \times 10^6$/mL. The CD8 cells comprised 8.1% of the starting material. Following enrichment, the nbuffy was 139 mL, with a total nucleated cell count of $24.2 \times 10^6$/mL of which 22.4% were CD8 positive. (recovery=78%)

Cells remaining in the tubing were pumped into the Treatment Bag 737 by operating the Buffy/Recirculation Pump 776 clockwise at 100 milliliters per minute for several seconds. The pump 776 was then stopped, the valve NEW4 796 was closed, and the valve NEW3 793 was opened, and the volume of collected buffy was determined by weight. The Treatment Bag 737 was agitated to mix the contents, and a sample was collected for coulter counter and flow cytometry analysis.

In this example, the number of cells in the treatment bag 791 was adjusted to $1 \times 10^9$, which is the number that could reportedly be captured using a single 5 mL vial of Dynabeads. Dynabeads were injected into the Treatment Bag 737, and the bead/cell mix was cycled through the Plate 778 and the Treatment Bag 737 by activating the Buffy/Recirculation Pump 776 clockwise. In this mode, the valves 1240, 1250, 790, 796, 772, and 798 are closed. The valves 791 and 793 are open. Hence circulation occurs through the treatment bag 737 to plate 778 via elements 793, 794, and 780. The magnet 1276 is disengaged from the plate 778. Circulation continues from the plate 778 through buffy pump 776, the HCT sensor 788, and valve 791 to the treatment bag 737. Hence, in this mode, the circulation through this pathway is counterclockwise. During this incubation period, cells expressing the specific cellular antigen (in this example CD8) are bound to the antibody coated Dynabeads. This incubation and circulation lasts at least 30 minutes, with mixing or agitation of the Treatment Bag 737 and the Plate 778.

When the antigen/antibody circulation step was complete, the Plate 778 was placed in a Dynal ClinExVivo MPC (the 8 kGauss magnet) 1276 with the magnet 1276 engaged. The Buffy/Recirculation Pump 776 continued pumping for several minutes to remove any Dynabeads from the tubing between the Plate 778 and the top of the Treatment Bag 737.

Once the line between the Plate 778 and the Treatment Bag 737 was clear, the pump 776 was stopped, the valve (NEW2) 791 was closed, the valve (NEW6) 1240 was opened, and the Buffy/Recirculation Pump 776 was then reactivated in the clockwise direction. This interrupted fluid communication into the treatment bag 737 by means of the valve 791 being closed. Circulation flowed from the treatment bag, through elements 793, 794, 780 to the plate 778, with the magnet 1276 engaged. All cells in the Treatment Bag 737 were pumped through the Plate 778. The Dynabead-cell complexes (CD8 positive or enriched fraction) were trapped in the plate 778 by the magnet 1276. Circulation continued from the plate 778, through the buffy pump 776 and HCT sensor 788 to the Waste Bag 1242 as the valve (NEW6) 1240 was opened. Thus, the remainder of the cells (negative fraction) flowed into the Waste Bag 1242.

When the Treatment Bag 737 was empty, the Buffy/Recirculation Pump 776 was stopped, the valve (NEW3) 793 was closed, the valve (NEW4) 796 was opened, and the pump 776 was reactivated in the same direction to allow the selection buffer from the bag 795 to flush the line from the bottom of the Treatment Bag 737, through the Plate 778, and to the Waste Bag 1242, ensuring that the majority of the cells remaining in the lines were processed.

When the lines had been flushed with buffer for several minutes, the Buffy/Recirculation Pump 776 was stopped, the valve (NEW6) 1240 was closed, the valve (NEW2) 791 is opened, and the Plate 778 is removed from the magnet 1276. Buffer from the bag 795 was added to the Plate 778 and the Treatment Bag 737 by cycling the Buffy/Recirculation Pump 776 clockwise. When sufficient buffer was added, the pump 776 was stopped, the valve (NEW4) 796 was closed, the valve (NEW3) 793 was opened, and the pump 776 was then restarted. The cell-bead mixture was circulated through the Plate 778 and the Treatment Bag 737 for several minutes to re-suspend the Dynabead-cell complexes. Circulation occurs through the treatment bag 737 to plate 778 via elements 793, 794, and 780. Circulation continues from the plate 778 through buffy pump 776, the HCT sensor 788, and valve 791 to the treatment bag 737. Hence, in this mode, the circulation through this pathway is counterclockwise. This step may be repeated and equates to washing the positive fraction to remove impurities.

Following washing, 2 ml of Dynal's DETACHaBEAD was injected into the Treatment Bag 737 and incubated with the Dynabead-cell complexes by activating the Buffy/Recirculation Pump 776 clockwise for at least 45 minutes. After incubation, the Plate 778 was placed in the magnet 1276. The Buffy/Recirculation Pump 776 was rotated clockwise for several minutes in order to clear any Dynabeads from the tubing between the Plate 778 and the top of the Treatment Bag 737. Once the line was clear of Dynabeads, the pump 776 was stopped, the valve (NEW2) 791 into the Treatment Bag 737 was closed, the valve (NEW1) 790 into the Collection Bag 786 was opened, and the Buffy/Recirculation Pump 776 was reactivated in the clockwise direction. Circulation occurs from the treatment bag 737 to plate 778 via elements 793, 794, and 780. Circulation continues from the plate 778 through buffy pump 776, the HCT sensor 788, and valve 790 to the Collection Bag 786. The magnet 1276 remained engaged with the plate 778.

Fluid and cells in the Treatment bag 737 were pumped through the Plate 778 and the Dynabeads (now detached from cells) were trapped by the magnet 1276 while the cells (positive selection) flowed into the Collection Bag 786. Any Dynabeads that were not captured by the main magnet 1276 should then be captured by the secondary magnet 1254, prior to entering the Collection Bag 786. When the Treatment Bag 786 was empty, the Buffy/Recirculation Pump 776 was stopped, the valve (NEW3) 793 was closed, the valve (NEW4) 796 was opened, and the pump 776 was then reactivated in the same direction. Buffer from the selection buffer bag 795 flushed the line from the bottom of the Treatment Bag 737, through the Plate 778, and to the Collection Bag 786, ensuring that the majority of the cells in the lines were processed.

When the lines had been flushed with buffer for several minutes, the Buffy/Recirculation Pump 776 was stopped. The Waste Bag 1240 and the Collection Bag 786 were weighed to determine collection volume, and the Waste Bag 1240 (negative fraction) was sampled for coulter counter, flow cytometry, and pH analysis. The enriched fraction in the Collection Bag 786 was concentrated and then sampled for coulter counter, flow cytometry, and pH analysis. The yield of CD8 positive cells was 33% and the purity was 92%.

Return of Non-Target Cells

Cells in the Waste Bag 1242 were concentrated for return to the patient represented by Patient Bag #2 (not shown in FIG. 12 but can be substituted for the bag 1206). All the valves in the system 1200 were closed except for valves (NEW5) 1250, (NEW6) 1240, (Green—Buffy Bottom) 798, (Pink—Plasma Top) 784, and (Return) 748, which were all open. This opened a path to transfer the contents of the Waste Bag 1242 into the bowl 730, with the overflow collected in the Return Bag 740. Thus, circulation from the waste bag 1242 was through valves 140 and 1250, air detector 794, valve 798 and pump 732 to the centrifuge bowl 730. From the bowl 730, circulation was via 784 into the return bag 740. This was accomplished by rotating the Red Cell Pump 732 counter-clockwise.

Once the Waste Bag 1240 was empty, the pump 732 was stopped and all valves were closed except for the valves (Blue—Plasma Bottom) 744, (Pink—Plasma Top) 784, and (Return) 748. All air in the bowl 730 was then purged by activating the Red Cell Pump 732 in a counter-clockwise direction at 20 milliliters per minute while simultaneously turning the centrifuge 730 on to a speed of 600-1000 RPM's for several seconds and then shutting centrifuge 730 down. This process of turning the centrifuge 730 on and off while the Red Cell Pump 732 was continuously pumping was repeated several times until no more air bubbles were seen leaving the bowl 730. Once complete, the centrifuge 730 was slowly ramped up to full speed with the pump 732 still activated, and the contents of the bowl 730 were allowed to separate for several minutes.

After separation had occurred, the Red Cell Pump 732 was stopped, valves (NEW2) 791 and (Yellow—Buffy Top) 772 were opened, and the valve (Pink—Plasma Top) 784 was closed. Counter-clockwise pumping of the Red Cell Pump 732 was resumed at 20 milliliters per minute. Circulation is from Return Bag 742 to Centrifuge Bowl 730 via the air detector 742, valve 774 and pump 732. From the bowl 730, circulation continues to the Treatment Bag via the valve 772, HCT sensor 788, and valve 791. This process removed the saline from the top of the bowl 730 while the majority of the non-target cells in the blood product remain in the bowl 730.

When the Return Bag 740 was empty, the centrifuge 730 was stopped and all the contents of the bowl 730 were returned to the Patient Bag #2 (not shown in FIG. 12) via the Red Cell Pump 732 clockwise and the Return Pump 746 counter-clockwise via the valve 748, air detector 750, pressure sensor 752, and return node 756. When the bowl 730 was emptied, both pumps 732 and 746 were stopped, the valve (Blue—Plasma Bottom) 744 was closed, the Saline valve 764 was opened, and the Return Pump 746 was reactivated counter-clockwise at 100 milliliters per minute for several seconds to flush the remaining non-target blood cells into the Patient Bag #2 (not shown in FIG. 12). The pump 746 was stopped and the Patient Bag #2 was weighed to determine the total volume and sampled for coulter counter and flow cytometry analysis. The non-target cells contained only 2.7% CD8 cells.

EXAMPLE 3

Collection of Mononuclear Cells and Enrichment of CD34+ Cells from Peripheral Blood Collection and enrichment of CD34+ cells can be conducted as described in Examples 1 and 2, using materials that specifically bind CD34.

Enrichment of CD34+ Cells from Collected Mononuclear Cells

In an embodiment of the invention, the subject can be mobilised with G-CSF. On completion of the standard CellEx mononuclear cell collection, the mononuclear cell product is washed with cell enrichment buffer PBS/EDTA (Miltenyi) supplemented with HSA and CD34+ selection beads (Miltenyi) introduced via the needle-free access port of the 'collection bag'. The mononuclear cell and bead mixture is incubated for 30 minutes with recirculation through the capture module of the modified CellEx disposable kit and terminated by displacing the cells via a peristaltic pump into the Miltenyi CliniMACS magnet system at approximately the manufacturer's suggested flow rate. CD34+ target cells can be enriched from non-target cells, and both target and non-target cell fractions can be collected in separate collection bags and further modified or returned to the patient.

Results

The Therakos CellEx Photopheresis System is capable of collecting a high yield of mononuclear cells and can be connected in a single fluid path to a cell enrichment system for the additional enrichment of target cells. Further improvements in the connection and interface between the collection and enrichment modules of the combined system may increase target cell recovery and yield.

EXAMPLE 4

Collection of Mononuclear Cells, Enrichment of CD4+ Cells from Peripheral Blood and Modification The cells of Example 1 or 2 can be modified in a closed fluid path as shown in FIG. 8. The enriched cells are transferred by means of a pump to the modification chamber. An agent such as a growth factor (example interleukin-2), peptides and/or a gene delivery agent (example viral vector) is introduced and the cells maintained at constant temperature (cultured). This causes the cells to alter in phenotype and/genotype and to have different physical and functional properties. The modified cells may be further cultured and used as therapeutic agents.

Notes on Hardware and Software Requirements

The pump deck remains virtually the same as existing CellEx, with an additional pump head to be added—there is room in the lower left corner of the pump deck.

If the globes and boards used for photopheresis are removed from CellEx, there is plenty of space to add what is required for selection and even modification. Additional bag hooks can be added to the left side of the instrument.

In the foregoing manner, a number of methods, apparatuses, and systems have been disclosed for processing blood cells. While only a small number of embodiments have been disclosed, it will be apparent to those skilled in the art in the light of this disclosure that numerous changes and substitutions may be made without departing from the scope and spirit of the invention.

The invention claimed is:

1. An apparatus for processing blood, said apparatus comprising:
    an inlet interface for coupling with a patient to receive blood directly from the circulation of said patient;
    a leukapheresis module coupled to said inlet interface for collecting bulk mononuclear blood cells from said received blood;
    an enrichment module coupled to said leukapheresis module for enriching concurrently target cells separated from non-target cells in said bulk mononuclear blood cells;
    a target-cell modification module adapted to provide gene modification coupled to at least one of said leukapheresis module and said enrichment module, said modification module modifying said enriched target cells;
    an outlet interface coupled to at least one of said leukapheresis module and said enrichment module for coupling with said patient to return enriched target cells to the circulation of said patient, said apparatus and said patient forming a closed loop when coupled together; and
    a controller for automated control of operation of said inlet and outlet interfaces, said leukapheresis module, and said enrichment module.

2. The apparatus as claimed in claim 1, wherein said controller comprises: a memory for storing data and instructions for automated control of operation of said inlet and outlet interfaces, said leukapheresis module, and said enrichment module; and a processor coupled to said memory capable of accessing said data and said instructions, said processor adapted to perform said instructions for automated control of operation of said inlet and outlet interfaces, said leukapheresis module, and said enrichment module.

3. The apparatus as claimed in claim 1, further comprising means for returning said modified target-cells to said patient.

4. The apparatus as claimed in claim 1, further comprising at least one pump for circulating at least a portion of said blood within said apparatus.

5. The apparatus as claimed in claim 4, further comprising a pump and at least one valve coupled to said inlet interface for providing said blood to said leukapheresis module and another pump and at least one valve coupled to said outlet interface for returning blood from said apparatus.

6. The apparatus as claimed in claim 1, wherein said leukapheresis module comprises a centrifuge bowl that uses differential centrifugation to collect said mononuclear blood cells.

7. The apparatus as claimed in claim 1, wherein said differential centrifugation is conducted by a continuous flow system.

8. The apparatus as claimed in claim 1, wherein the target cells are hematopoietic progenitor cells.

9. The apparatus as claimed in claim 1, wherein the target cells are mesenchymal cells.

10. The apparatus as claimed in claim 1, wherein the target cells are T lymphocytes.

11. The apparatus as claimed in claim 1, wherein the target cells are B lymphocytes.

12. The apparatus as claimed in claim 1, wherein the target cells are monocytes.

13. The apparatus as claimed in claim 1, wherein the target cells are dendritic cells.

14. A system for processing blood, said system comprising:
    means for obtaining blood from a patient; and
    a single blood processing device coupled to said obtaining means and said patient to form a closed loop between said patient and said blood processing device, said blood processing device comprising:
    means for collecting bulk mononuclear blood cells from said blood by leukapheresis implemented using said blood processing device in said closed loop;

means for enriching concurrently target cells separated from nontarget cells in said bulk mononuclear blood cells using said blood processing device in said closed loop; and means for genetically modifying target cells in said closed loop.

15. The system as claimed in claim 14, further comprising means for discarding said non-target cells.

16. The system as claimed in claim 14, further comprising means for concurrently monitoring the collecting and enriching of said collecting and enriching means, respectively.

17. The system as claimed in claim 14, wherein said collecting means uses differential centrifugation to collect said mononuclear blood cells and said enriching means uses ligand capture to enrich said target cells.

18. The system as claimed in claim 17, wherein said ligand is an antibody specific for a cell surface ligand.

19. The system as claimed in claim 14, wherein the target cells are hematopoietic progenitor cells.

20. The system as claimed in claim 14, wherein the target cells are mesenchymal cells.

21. The system as claimed in claim 14, wherein the target cells are T lymphocytes.

22. The system as claimed in claim 14, wherein the target cells are B lymphocytes.

23. The system as claimed in claim 14, wherein the target cells are monocytes.

24. The system as claimed in claim 14, wherein the target cells are dendritic cells.

* * * * *